US012588929B2

(12) United States Patent
Bacich et al.

(10) Patent No.: US 12,588,929 B2
(45) Date of Patent: Mar. 31, 2026

(54) APPARATUS AND METHOD FOR EVERTING CATHETER FOR EMBRYO TRANSFER USING TRANSVAGINAL ULTRASOUND

(71) Applicant: CrossBay Medical, Inc., San Diego, CA (US)

(72) Inventors: Steven R. Bacich, Half Moon Bay, CA (US); Matthew Thomas Yurek, San Diego, CA (US); Cristiano Danilo Maria Fontana, Milan (IT); Piush Vidyarthi, San Rafael, CA (US)

(73) Assignee: CrossBay Medical, Inc., San Diego, CA (US)

( * ) Notice: Subject to any disclaimer, the term of this patent is extended or adjusted under 35 U.S.C. 154(b) by 56 days.

(21) Appl. No.: 18/633,344

(22) Filed: Apr. 11, 2024

(65) Prior Publication Data

US 2024/0252209 A1      Aug. 1, 2024

Related U.S. Application Data

(63) Continuation of application No. 16/898,090, filed on Jun. 10, 2020, now abandoned.

(51) Int. Cl.
| | |
|---|---|
| *A61B 17/425* | (2006.01) |
| *A61B 17/43* | (2006.01) |
| *A61B 17/435* | (2006.01) |
| *A61M 25/01* | (2006.01) |

(52) U.S. Cl.
CPC ............ *A61B 17/425* (2013.01); *A61B 17/43* (2013.01); *A61B 17/435* (2013.01); *A61M 25/0119* (2013.01); *A61M 2210/1433* (2013.01)

(58) Field of Classification Search
CPC ... A61B 17/425–435; A61D 19/00–04; A61M 2210/14–1475; A61M 25/0119
See application file for complete search history.

(56) References Cited

U.S. PATENT DOCUMENTS

| | | | |
|---|---|---|---|
| 3,421,509 | A | 1/1969 | Fiore |
| 3,911,927 | A | 10/1975 | Rich et al. |
| 4,606,347 | A | 8/1986 | Fogarty et al. |
| 4,863,440 | A | 9/1989 | Chin |
| 5,074,845 | A | 12/1991 | Miraki et al. |
| 5,346,498 | A | 9/1994 | Greelis et al. |

(Continued)

FOREIGN PATENT DOCUMENTS

| | | |
|---|---|---|
| GB | 2391815 | 2/2004 |
| WO | WO 2019/046800 | 3/2019 |
| WO | WO 2019/118520 | 6/2019 |

*Primary Examiner* — Thaddeus B Cox
(74) *Attorney, Agent, or Firm* — Levine Bagade Han LLP

(57) ABSTRACT

Everting balloon systems and methods for using the same with an alignment element for stability and anti-rotation of the everting balloon are disclosed herein. The systems can be configured to access and deliver instruments, media, or other catheters into bodily lumens and cavities. The alignment element can eliminate the potential for the everting membrane to become twisted or rotated which could impact access or the ability of the system to deliver materials. A compliance member can facilitate internal pressurization of the everting catheter system. An everting catheter system can be configured for use with transvaginal ultrasound and a lower profile speculum is described.

6 Claims, 35 Drawing Sheets

(56)             References Cited

U.S. PATENT DOCUMENTS

| | | | |
|---|---|---|---|
| 5,364,345 A | 11/1994 | Lowery et al. | |
| 5,372,247 A | 12/1994 | Nishikawa | |
| 5,374,247 A | 12/1994 | Lowery et al. | |
| 5,383,889 A | 1/1995 | Warner et al. | |
| 5,458,573 A | 10/1995 | Summers | |
| 5,472,419 A | 12/1995 | Bacich | |
| 5,630,797 A | 5/1997 | Diedrich et al. | |
| 5,902,286 A | 5/1999 | Reitz | |
| 5,993,427 A | 11/1999 | Rolland et al. | |
| 6,039,721 A | 3/2000 | Johnson et al. | |
| 6,953,460 B2 | 10/2005 | Maguire et al. | |
| 9,028,401 B1 | 5/2015 | Bacich et al. | |
| 10,034,986 B2 | 7/2018 | Yurek et al. | |
| 2013/0060234 A1* | 3/2013 | Besser | A61M 25/1006 |
| | | | 604/509 |
| 2015/0133727 A1 | 5/2015 | Bacich et al. | |
| 2015/0142045 A1 | 5/2015 | Bacich et al. | |
| 2019/0009058 A1 | 1/2019 | Bacich et al. | |
| 2020/0297384 A1 | 9/2020 | Bacich et al. | |

* cited by examiner

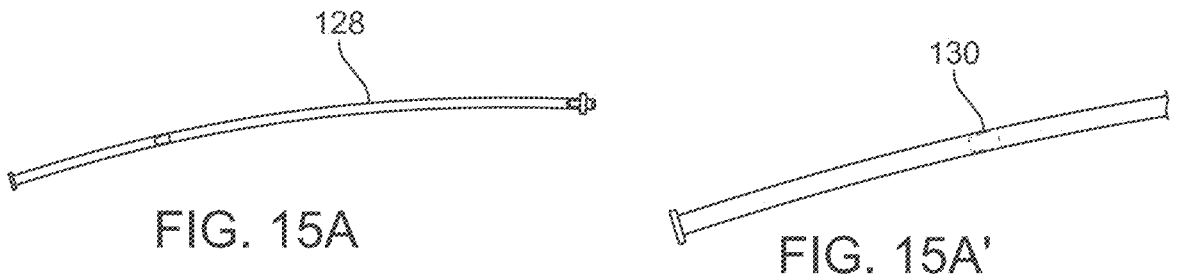
FIG. 15A
FIG. 15A'
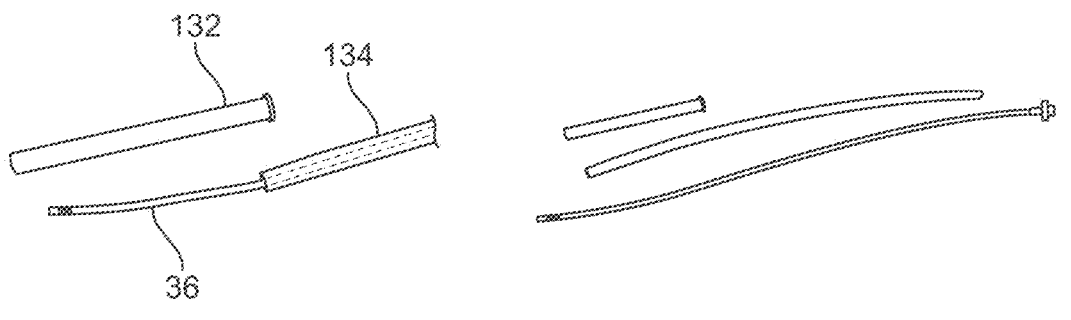
FIG. 15B
FIG. 15B'
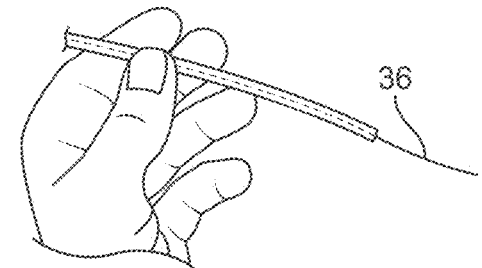
FIG. 15B"

NOT INVENTION

Anterior lip
of cervix

Anterior fornix          Left vaginal
of vagina                    wall

Cervical
os

Right vaginal
wall

Posterior
fornix
of vagina

Posterior
lip of cervix

Cuscoe's
speculum

NOT INVENTION

NOT INVENTION

NOT INVENTION

NOT INVENTION

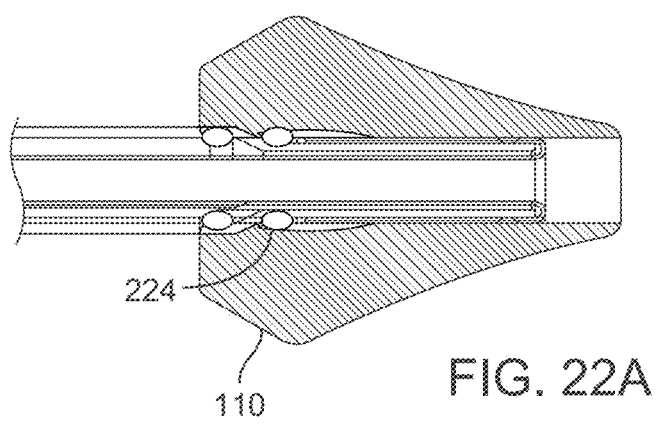
224
110
FIG. 22A
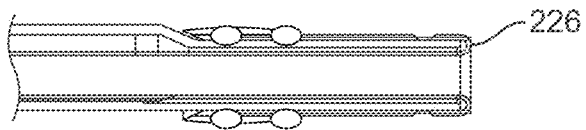
226
FIG. 22A'
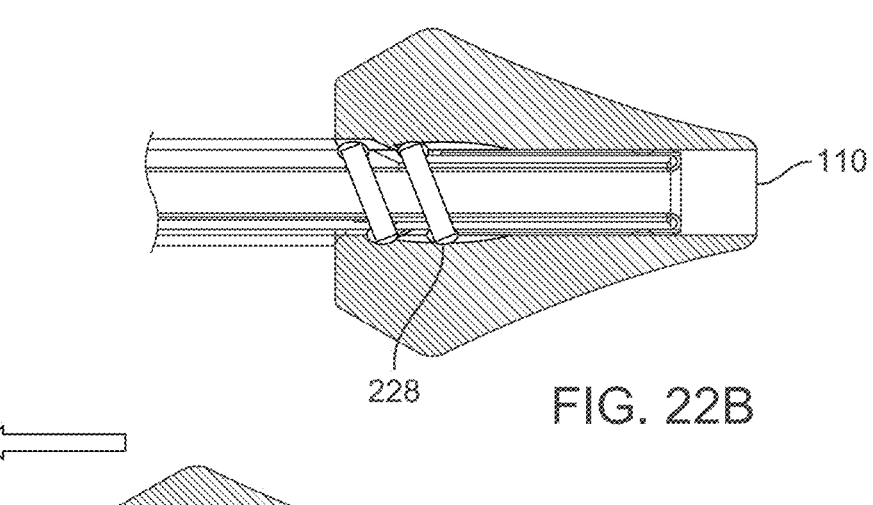
110
228
FIG. 22B
228
226
FIG. 22B'

APPARATUS AND METHOD FOR EVERTING CATHETER FOR EMBRYO TRANSFER USING TRANSVAGINAL ULTRASOUND

CROSS-REFERENCE TO RELATED APPLICATIONS

This application is a continuation of U.S. patent application Ser. No. 16/898,090 filed Jun. 10, 2020, now abandoned, which is a continuation of International Patent Application No. PCT/US2018/065046 filed Dec. 11, 2018, which claims priority to U.S. Provisional Application No. 62/597,353 filed Dec. 11, 2017, which are incorporated by reference herein in their entireties.

BACKGROUND

This disclosure can be used for everting catheters that can have an inner catheter, outer catheter, and everting membrane that can be connected to both catheters. The inner catheter may contain an inner lumen to pass fluid or media, drugs or therapeutic agents, instruments or devices, and other catheters.

For physicians and medical professionals, accessing systems for vessels and bodily cavities in patients have typically used various guidewire and catheter technologies or everting catheters. Everting catheters utilize a traversing action in which a balloon is inverted and with the influence of hydraulic pressure created by a compressible or incompressible fluid or media, rolls inside out or everts with a propulsion force through the vessel. Everting balloons have been referred to as rolling or outrolling balloons, evaginating membranes, toposcopic catheters, or linear everting catheters such as those in U.S. Pat. Nos. 5,364,345; 5,372,247; 5,458,573; 5,472,419; 5,630,797; 5,902,286; 5,993,427; 6,039,721; 3,421,509; and 3,911,927; all of which are incorporated herein by reference in their entireties. These are categorized as everting balloons and are for traversing vessels, cavities, tubes, or ducts in a frictionless manner. In other words, an everting balloon can traverse a tube without imparting any shear forces on the wall being traversed. Because of this action and lack of shear forces, resultant trauma can be reduced and the risk of perforation reduced. In addition as a result of the mechanism of travel through a vessel, material and substances in the proximal portion of the tube or vessel are not pushed or advanced forward to a more distal portion of the tube or vessel.

In addition, as the everting catheter deploys inside out, uncontaminated or untouched balloon material is placed inside the vessel wall. In the inverted or undeployed state, the balloon is housed inside the catheter body and cannot come into contact with the patient or physician. As the balloon is pressurized and everted, the balloon material rolls inside out without contacting any element outside of the vessel. Another advantage of an everting balloon catheter is that the method of access is more comfortable for the patient since the hydraulic forces "pull" the balloon membrane through the vessel or duct as opposed to a standard catheter that needs to be "pushed" into and through the vessel or duct.

Everting catheters have been described as dilatation catheters. Representative examples of dilating everting catheters include U.S. Pat. Nos. 5,364,345 and 4,863,440, both of which are incorporated by reference herein in their entireties.

Everting catheters have also been described with additional elements such as a handle for controlling instruments within an everting catheter. A representative example is U.S.

Pat. No. 5,346,498 which is incorporated by reference herein in its entirety. Everting balloon catheters can be constructed with an inner catheter with an internal lumen or through-lumen (or thru-lumen). The through-lumen can be used for the passage of instruments, media, materials, therapeutic agents, endoscope, guidewires, or other instruments. Representative samples of everting catheters with through-lumens are in U.S. Pat. Nos. 5,374,247 and 5,458,573. In addition, everting catheters have been described with waists or a narrowing of the balloon diameter, such as in U.S. Pat. No. 5,074,845, which is incorporated by reference herein in its entirety.

Furthermore, infertility is a condition that affects 1 out of 8 couples in the US. One of the early treatments in the infertility regime is insemination. Intrauterine insemination or IUI is a very common procedure since it is in the early work up of an infertile couple. Most assisted reproductive clinics perform at least 3 IUI cycles before trying more expensive treatment options such as IVF.

Also, when delivering the reproductive material, such as an embryo, into the uterine cavity, vacuum effect can unintentionally remove the reproductive material from the uterine cavity. In existing systems, when the transfer catheter is retracted from a second outer or guiding catheter (e.g., the "inner" catheter), the retraction produces vacuum pressure within the uterine cavity. This vacuum pressure is created in the uterine cavity by the removal and backward movement of the transfer catheter within the inner catheter. After the embryo transfer is completed, an embryologist may inspect the transfer catheter to verify that the embryos or reproductive material was indeed deposited in the uterus and not pulled back into the transfer catheter because of the vacuum effect. The same procedure may be done for the outer catheter once this catheter is removed.

The passage of the embryo transfer catheter may become impeded if the everting membrane is rotated or twisted. Twists within the balloon membrane can also reduce the ability of the everting membrane to traverse a lumen or cavity or unroll as intended. A twist in the balloon membrane can occur if the inner catheter is rotated about its central axis in relation to a stationary outer catheter. By rotating the inner catheter, the balloon membrane which is connected between both the outer catheter and inner catheter becomes twisted. In this particular situation of an everting balloon, twists in the balloon membrane can significantly impact performance of the everting system.

A twist in the everting membrane can occur during use or prep of the catheter prior to inserting the device within a patient. A twist in the everting membrane can also occur when a catheter system has the requirement of multiple eversions and retractions to complete a procedure within a patient. Likewise, a twist in the balloon system can unintentionally occur as a byproduct of the manufacturing process.

In the device configuration using a handle system, an anti-rotation feature can be particularly advantageous. As described previously, handles are very useful for driving the inner catheter and controlling the advancement and retraction of instruments, other catheters, media, and materials within the inner catheter lumen. Manipulation of a handle can inadvertently rotate the inner catheter system within the outer catheter and thereby creates twists in the balloon membrane. This situation can be exasperated by the introduction and removal of multiple instruments and devices within the inner catheter lumen.

Having an everting catheter system in which twists or inadvertent rotations of the balloon membrane will enable more stable and secure use of an everting catheter. An untwisted balloon membrane provides the least obstructed passage within the everting system. Some everting catheter systems will be more prone to balloon twisting due to the length of the balloon membrane and inner catheter and type of balloon membrane material. In some clinical applications, more tortuous anatomy may instigate a greater likelihood of balloon twists as a result of the manipulations the clinician may need to perform to complete the procedure or obtain access to the desired target location in the body.

Maintaining the alignment of the inner catheter, outer catheter, and balloon membrane may be accomplished through a handle and ratchet system as described previously. The alignment feature is accomplished by the ratchet and handle that prevents rotation of the inner catheter. The systems described herein are directed towards internal catheter apparatus that provide alignment or anti-rotation capability without requiring an additional set of components like rails, tracks, ratchets, or handles on the exterior for the catheter system.

Another clinical issue with an everting catheter is that physicians may inadvertently pull or elongate the inner catheter upon inversion of the balloon membrane. Over-elongation can stretch the balloon membrane or damage the catheter components. A feature that mechanically prevents this from occurring will be a benefit to the catheter system.

Another problematic issue for everting catheters is the pressurization step in prepping the catheter. One option that is described in the prior art is the use of an inflation device with pressure gauge that indicates the internal pressure of the catheter system. Inflation devices with pressure gauges, or building an integral pressure gauge within the catheter system, can be expensive. Using a separate, reusable pressure gauge adds to the number of components required for performing the procedure. Having a simple mechanism that regulates and indicates the amount of pressure within the catheter system would be a benefit. For more specialized procedures, being able to modulate the internal pressure depending upon the medical procedure could be particularly advantageous.

For everting catheters used in IVF procedures, it is beneficial to stabilize the inner catheter when full eversion is completed for two-stage embryo transfer procedures. A two-stage embryo transfer is performed by everting the membrane across the endocervical canal and into the uterine cavity and subsequently placing the loaded embryo transfer catheter through the inner catheter and ultimately within the uterus. This operation is done in two steps and the infertility specialist will inform the embryologist that the inner catheter has been everted and is now in place within the uterine cavity. The embryologist will then aspirate and load the embryo or embryos into the distal end of the embryo transfer catheter for eventual insertion through the inner catheter for deposition in to the uterine cavity. This is the completion of the second stage of the process. During the loading step performed by the embryologist, a mechanism that stabilizes and indicates to the user that the inner catheter is in position would be a benefit.

Another problem with everting catheters is preparing the system by internal pressurization. This preparation step can vary among users and over-pressurization, and under-pressurization, of the everting system can negatively impact the performance of the device.

Accessories can be used by the embryologist and physician performing the transfer procedure to handle the embryo transfer catheter.

The embryo transfer procedure can be done with transvaginal ultrasound (TUS). In current medical practice, the significant majority of IVF procedures are performed using abdominal ultrasound over TUS, or no ultrasound visualization at all. TUS in most practitioners' hands provides greater or enhanced visibility of the IVF catheters and procedure in general than abdominal ultrasound since the ultrasound transducer is closer in physical proximity to the catheters or uterus (the visualization target) in situ. Secondly, abdominal ultrasound may need to penetrate through varying amounts or layers of adipose or fat tissue. To overcome this situation in more obese women, the ultrasound technician needs to push the abdominal probe deeply into the tissue of the female patient's stomach to obtain sufficient views which can be uncomfortable or painful for the patient. Thirdly, to facilitate the visualization of the catheters in the uterine cavity, women are instructed prior to the procedure to maintain a full bladder for the entire procedure. In some cases if the visualization is not sufficient, female patients are asked to consume more fluids and the procedure is delayed to allow for time for urine to be created, instilled, and visible in the bladder. And finally, abdominal ultrasound requires an ultrasound technician, nurse, physician, or additional pair of hands to manipulate the abdominal ultrasound during the actual IVF procedure. In some situations the IVF physician will need to obtain the abdominal ultrasound image and then pass off or release the abdominal ultrasound probe to the technician, nurse, or other physician so that the IVF catheterization procedure can be performed. As such, for all of the reasons mentioned above, the ability to perform IVF procedures more easily using TUS would be a benefit to patients and physicians. Another area to facilitate IVF procedures would be to allow the physician to use both instruments without requiring or necessitating an additional pair of hands to complete the procedure. This is particularly true with TUS since it would enhance the procedure if the physician manipulating the catheters, and directing the ultrasound imaging, was the same physician. Having a mechanism that allows the physician performing IVF with TUS to couple the everting catheter, or IVF catheter in general, to the TUS probe so that the contralateral hand of the physician could advance the embryo transfer catheter would be advantageous.

Another area of improvement would be to automate the translation and/or retraction of the inner catheter without requiring the physician to use two hands to complete the movements. A manual controller that is operated by one hand can be coupled to the everting catheter system or a mechanism that automatically translates and/or retracts the inner catheter.

Another area of improvement for IVF and uterine procedures in general would be a modified type of speculum that is more comfortable for the patient. This is particularly true for IVF procedures since it has been reported in medical literature that the act of placing a speculum in a patient by itself create the nidus for uterine contractions. For IVF, the ability to perform the procedure with a specific speculum that is easily adjustable for directed viewing of the exocervix, can be directed for specific lateral wall viewing, can become low profile for the insertion of other devices like TUS probe, and facilitates the use of an everting IVF catheter, or any IVF catheter in general, would be a benefit. This specific speculum can work as a system with the IVF catheter or any intravaginal or transvaginal procedure separately without an everting catheter or catheters in general and instead would provide a lower profile speculum for visualizing the vagina.

SUMMARY

An everting balloon system is disclosed that can be used for uterine access procedures. The everting balloon system can be used for IVF and intrauterine insemination procedures, urinary incontinence diagnostic and therapeutic procedures, delivering intra-fallopian tube inserts, media, or diagnostic instruments, dilation of a body lumen, for access and sealing within a body cavity, or combinations thereof. The system can have a handle for insertion. The everting catheter system can be used for TUS IVF procedures. The everting catheter system can have mechanisms that automatically translate and/or retract the inner catheter which is coupled to the everting membrane. A speculum can be used with everting catheters and other transvaginal catheter procedures.

The everting balloon system can be used to access the uterus, bladder, ureters, kidneys, ducts, vessels of the vasculature, nasal passageways, other bodily lumens, or combinations thereof. Devices, tools, instrumentation, endoscopes, drugs, therapeutic agents, sampling devices (brushes, biopsy, and aspiration mechanisms), or combinations thereof can be delivered through the inner catheter lumen to the target site.

The everting balloon system can have an internal alignment mechanism that prevents rotation and spinning of the balloon membrane.

The everting balloon system can have an internal mechanism that prevents over-elongation of the inner catheter during balloon inversion.

The everting balloon system can have a compliant pressurization apparatus that's provides a pre-determined pressure within the catheter system with an indicator to the user that system is at the appropriate operating pressure.

Another embodiment can automatically pressurize the everting balloon system to a predetermined amount.

The everting balloon system can have an integral pressurization system that provides an indicator and the ability to quickly shift the pressurization state of the balloon system from pressurized to non-pressurized. Intermediate degrees of pressurization can also be selected.

The everting balloon system can have a mechanism that stabilizes the inner catheter at the full eversion stage and provides an indicator to the user that catheter system is at the appropriate step in the process for embryo transfer.

The everting balloon system can have a proximal hub connector that aids the physician and embryologist in delivering the embryo transfer catheter to the delivery catheter.

The everting balloon system can be shaped with distal end features that facilitate uterine access without the need for a speculum and/or tenaculum.

The everting catheter system can have accessories that make the handling of the embryo transfer catheter easier.

The everting catheter system can be coupled to the TUS probe to allow for simultaneous ultrasound visualization of the catheterization procedure in situ and manipulation of the catheters.

The everting catheter system can have mechanisms that automatically translate and/or retract the inner catheter coupled to the everting membrane.

The everting catheter system that can couple to a speculum that facilitates handling of the catheter system in the vagina. The speculum itself can be used with or without the everting catheter system for other transvaginal procedures.

The everting catheter system can have controllers for both the inner catheter coupled to the everting membrane and a controller for the embryo transfer catheter, or the same controller can perform both functions.

The everting catheter system can have an acorn tip at the distal end that can be malleable or articulate to enter into the exocervical os. The acorn tip can also be detachable or retractable to reveal a penetrating tip to further guide the everting membrane into the exocervical os.

The TUS IVF procedure can have a specific speculum which provides a stable platform for the physician to hold and position the IVF catheters or devices.

The IVF procedures can use an everting catheter, a handle mechanism can be incorporated that can allow for one-handed advancement or translation of both the inner catheter coupled to the everting balloon, and the advancement of the embryo transfer catheter. Such a system can allow the physician to maintain control of the TUS at all times for both the advancement of the everting balloon catheter and the advancement of the embryo transfer catheter.

The distal end of the everting catheter which engages the exocervix can be a distal tip acorn tip that articulates or can be malleable to be directed towards the exocervix os or opening. A detachable or retractable acorn tip that exposes a more guiding or penetrating distal nozzle of the outer catheter that facilitates entry into the cervix can be used.

The embryo transfer procedures can be performed with transvaginal ultrasound. The disclosed systems and methods can be used and performed without a speculum, for example, for patient comfort.

BRIEF DESCRIPTION OF THE DRAWINGS

FIGS. 15A and 15A' illustrate a protective tube system for the embryo transfer catheter that facilitates handling and transport of the catheter.

FIGS. 15B, 15B', and 15B" illustrate a protective tube system for the embryo transfer catheter in the detached configuration for the loading of embryos.

FIG. 18B illustrates a speculum in use.

FIG. 21' illustrates an acorn tip at the distal end of an everting catheter that can be articulatable.

FIG. 22A is a cross-sectional view of a variation of the distal end of an everting catheter that has an acorn tip that is detachable.

FIG. 22A' is a cross-sectional view of the variation of the distal end of an everting catheter of FIG. 22A with the acorn tip removed to reveal a penetrating member for insertion into the exocervical os.

FIG. 22B is a cross-sectional view of a variation of the distal end of an everting catheter that has a retractable acorn tip.

FIG. 22B' is a cross-sectional view of the variation of the distal end of an everting catheter of FIG. 22B with the acorn tip retracted to reveal a penetrating member for insertion into the exocervical os.

DETAILED DESCRIPTION

Figures 1A, 1B, 1C, 1D, 1E:
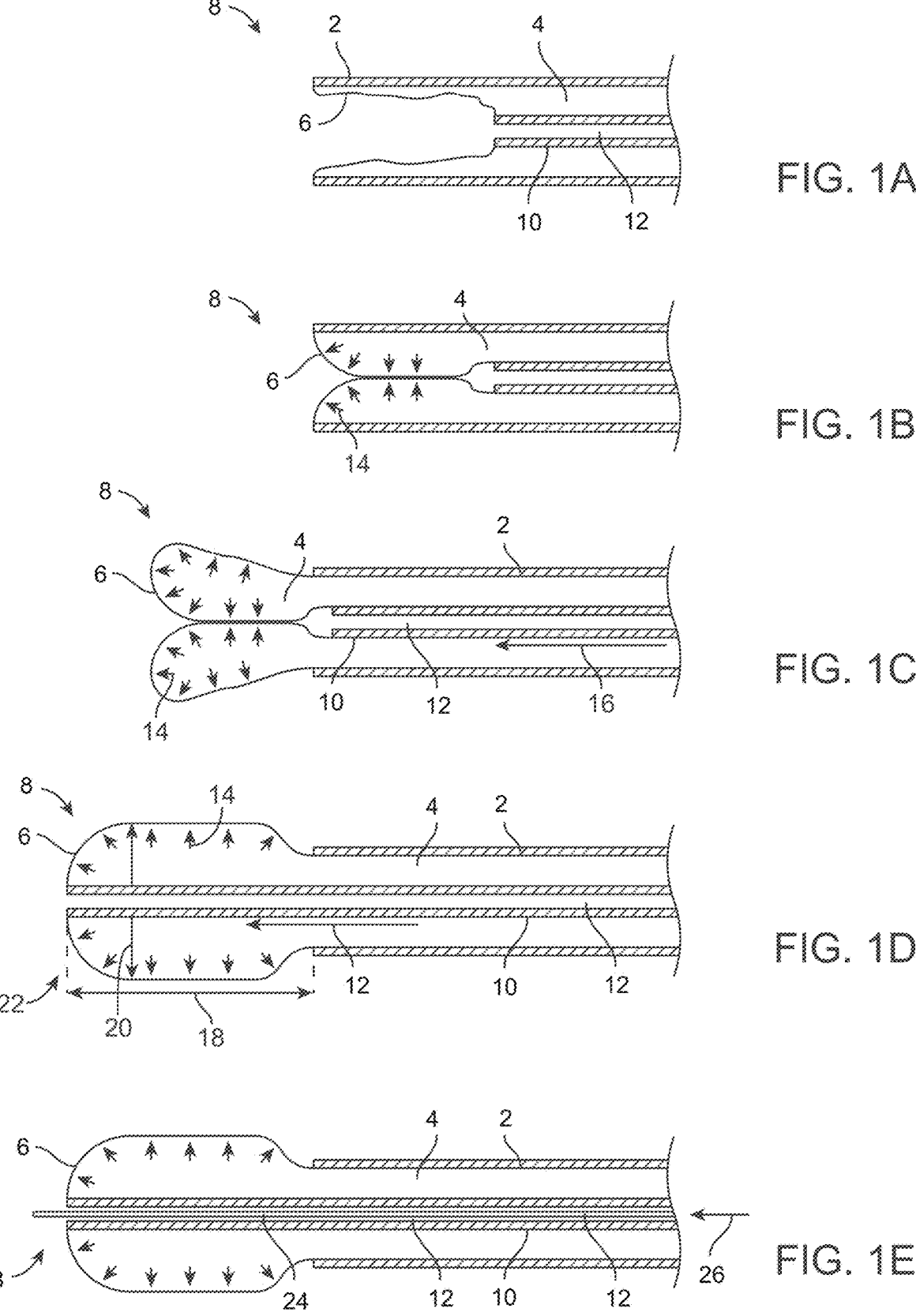
FIGS. 1A through 1E are longitudinal cross-sectional views of the distal end of a variation of a method for using the everting balloon system.

An everting balloon system 8 (also referred to as an everting catheter system 106) that can be used to traverse a vessel, such as the cervical canal is disclosed. The everting balloon system 8 can be used to access the uterine cavity via the cervix. The cervical canal is a single lumen vessel that can stretch or dilate. The everting balloon system 8 can have a control system that can be operated with one hand. The pressurization states or configurations of the everting catheter system 106 can be changed and controlled with one hand of the user.

FIGS. 1A through 1E illustrate that an everting catheter system 106 can have a radially outer catheter 2, a balloon membrane 6, and a radially inner catheter 10. The inner catheter 10 can have an inner catheter lumen 12 (e.g., a through-lumen). The distal end of the inner catheter lumen 12 can be open or closed. The inner catheter 10 can have the inner catheter lumen 12, or be a solid rod or flexible mandrel, or contain multiple lumens for the delivery of other agents, tools, catheters, instruments, endoscopes, and other media. The inner catheter 10 can be made from multiple polymeric materials and have a more flexible distal end and more rigid proximal end. Distal end flexibility can be enhanced with the incorporation of a distal end coil or spring 150 to provide distal end flexibility and support from kinking the lumen of the inner catheter 10. The internal lumen of the inner catheter 10 can be made from a lubricious material such as Teflon or coated with a lubricious coating to facilitate the passage of instruments, tools, or other catheters through the internal lumen.

The everting balloon system 8 can have a media volume 4. The media volume 4 can be the contiguous open volume between the inner catheter 10 and outer catheter 2 that is proximal to the balloon membrane 6. A radially outer terminal perimeter of the balloon membrane 6 can be attached to the distal terminal end of the outer catheter 2. A radially inner terminal perimeter of the balloon membrane 6 can be attached to the distal terminal end of the inner catheter 10.

FIG. 1A illustrates that the everting catheter system 106 can be in an unpressurized configuration. The media volume 4 can be uninflated and unpressurized. The balloon membrane 6 can be slack.

FIG. 1B illustrates that that everting catheter system 106 can be in a pressurized and uneverted configuration. A pressurization device, such as a pump, for example at the proximal end of the everting catheter system 106 can be in fluid communication with the media volume 4. The pressurization device can deliver a fluid media, such as a pneumatic gas or hydraulic liquid media (e.g., saline, water, culture media, air, carbon dioxide, air-infused fluids, carbonated fluids, or combinations thereof), at a media pressure 14 to the media volume 4. The media pressure 14 in the everting balloon 22 can be from about 2 to about 5 atmospheres of pressure when in the everted configuration and higher media pressures 14 from about 5 atmospheres to 10 atmospheres are possible, for example, to provide greater everting capability for more difficult or stenotic passageways in the body.

The balloon membrane 6 can inflate and be in tension. The balloon membrane 6 can block the distal port of the inner catheter lumen 12.

The everting catheter system 106 can have an everting catheter system distal end 210 and an everting catheter system proximal end 214.

FIG. 1C illustrates that the everting catheter system 106 can be in an inflated and partially everted configuration. The inner catheter 10 can be translated distally, as shown by arrow 16, with respect to the outer catheter 2, and out of the outer catheter 2. The distal terminal end of the inner catheter 10 can be proximal of the distal terminal end of the balloon membrane 6. The distal terminal end of the inner catheter 10 can be proximal or terminal of the distal terminal end of the outer catheter 2. The balloon membrane 6 can block the distal port of the inner catheter lumen 12 or can be open allowing fluid communication between the inner catheter lumen 12 and the target site.

FIG. 1D illustrates that the everting catheter system 106 can be in an inflated, fully everted, and fully distally extended configuration. The inner catheter 10 can be translated distally, as shown by arrow 16, with respect to the outer catheter 2 until the distal terminal end of the inner catheter 10 is longitudinally beyond or co-terminal with the distal terminal end of the balloon membrane 6. The distal port of the inner catheter lumen 12 can be unobstructedly accessible and in fluid communication with the target site.

In the fully inflated configuration, the balloon membrane 6 can form an inflated everting balloon 22. The everting balloon 22 can have a balloon outer diameter 20 and balloon length 18 in the inflated and fully everted configuration.

The balloon outer diameter 20 can be from about 2 mm to about 20 mm, more narrowly from about 2 mm to about 7 mm, for example about 3.0 mm. The outer diameter can be constant or vary along the length of the everting balloon 22. For example, for use in the cervical canal, the most proximal portion of the everting balloon outer diameter 22 could be configured with a smaller outer diameter than the remainder of the everting balloon membrane 6. As an example, the first proximal portion of the everting balloon 22 can have a smaller balloon outer diameter 20 such as from about 2 mm to 4 mm for a length of from about 5 mm to about 10 mm from the distal terminal end of the outer catheter 2, and the remainder of the length (e.g., from about 4 cm to about 7 cm along the everting balloon 22) of the everting balloon 22 can have a balloon outer diameter 20 from about 4 mm to about 7 mm.

The interior surface and lumen of the balloon can be coated with a lubricious material to facilitate rolling and unrolling of the interior surfaces of the everting balloon membrane 6.

The exterior surface of the balloon membrane 6 can be configured with ridges, projections, bumps, grooves, and additional surface or mechanical features, or combinations thereof, for example for increased friction or holding power within the vessel.

The everting balloon 22 length 18 can be from about 2 cm to about 10 cm, more narrowly from about 3.5 cm to about 8.5 cm (e.g., for use in a longer uterine cavity lengths), yet more narrowly from about 5 cm to about 7.5 cm.

FIG. 1E illustrates that the everting catheter system 106 can be in an inflated and partially or fully everted configuration. A tool, liquid, gas, or combinations thereof can be translated, as shown by the arrow, through the inner catheter lumen 12, out of the distal port of the inner catheter lumen 12 and into the target site. The tool 24 can be a biopsy tool, a scope, a sonogram probe, a plug, a cauterization tool, or combinations thereof. Suction can be applied from the proximal end of the inner catheter lumen 12, and to the target site, for example removing debris from the target site through the inner catheter lumen 12. For use in IVF procedures, an embryo transfer catheter 28 is translated through the inner catheter lumen 12 for deposition of embryo(s) or other reproductive material such as gametes or sperm.

To retract and reposition or remove the balloon membrane 6, the inner catheter 10 can be pulled proximally to pull the balloon membrane 6 back within the outer catheter 2. The balloon membrane 6 can be deflated or have media pressure 14 reduced and the entire system can be withdrawn from the target site.

Figure 2A:
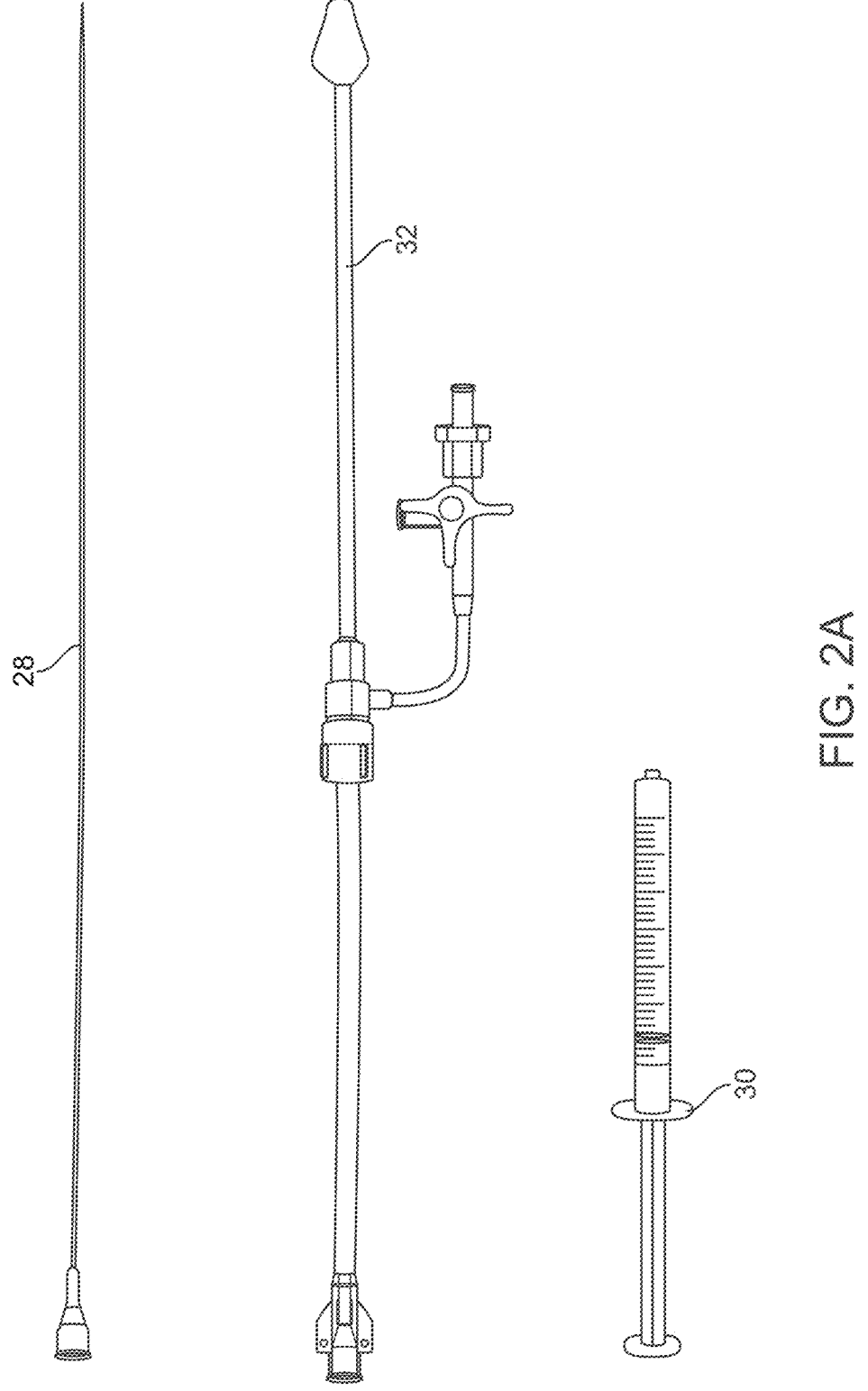
FIG. 2A illustrates an everting balloon system with a delivery catheter, embryo transfer catheter, and a pressurization syringe.
Figures 2B, 2C:
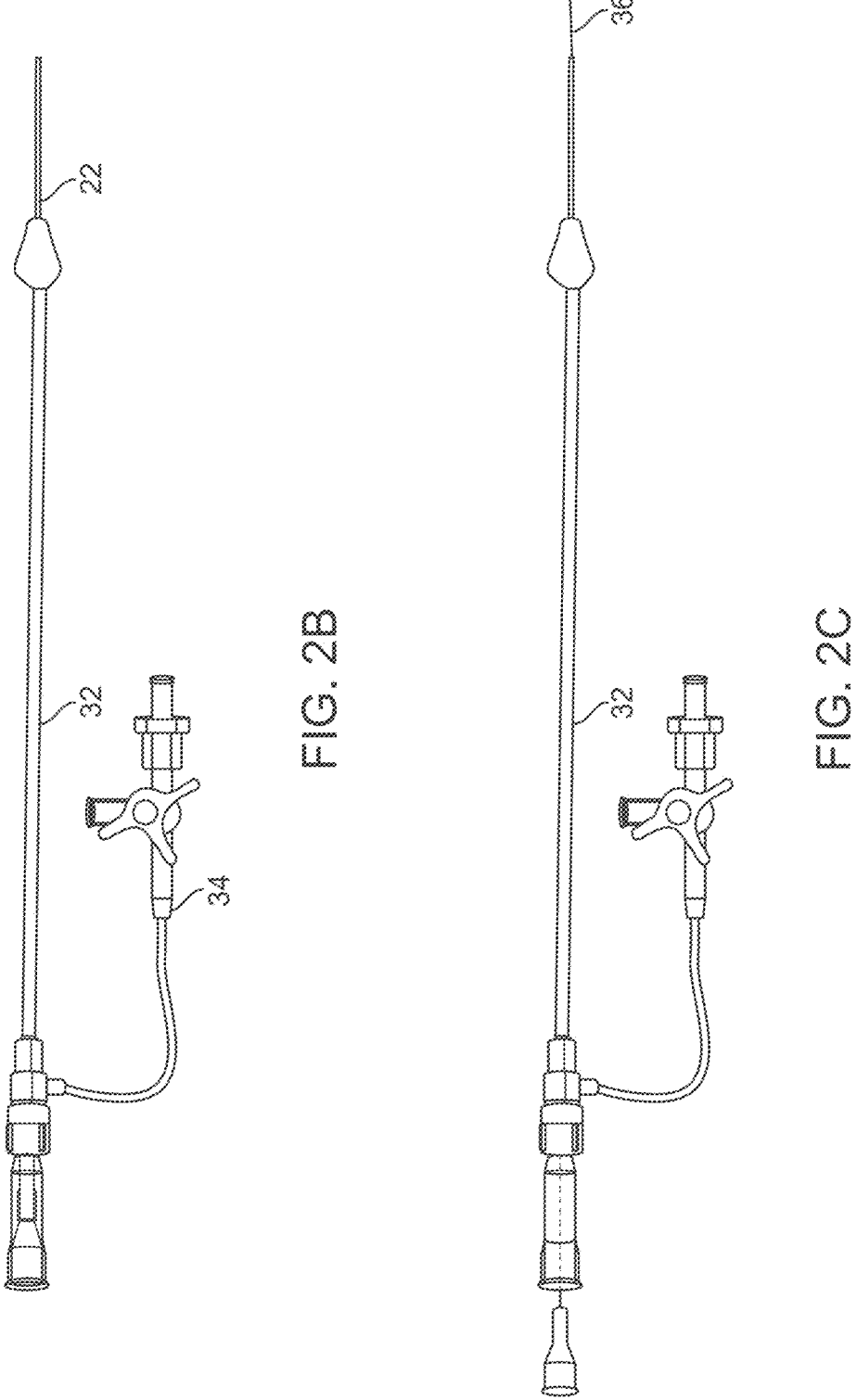
FIG. 2B illustrates a variation of the everting balloon system in a fully everted configuration.
FIG. 2C illustrates an embryo transfer catheter beyond the distal end of the everting balloon membrane.

FIG. 2A illustrates an everting balloon system 8 that can have a delivery catheter 32, embryo transfer catheter 28, and a pressurization syringe 30. The embryo transfer catheter 28 can be translatably slid into and/or partially through the delivery catheter 32 (e.g., with the distal end of the embryo transfer catheter 28 extending out of the distal terminal end of the delivery catheter 32). The pressurization syringe 30 can be detachably connected or attached to the proximal terminal end (e.g., at a luer lock) of the delivery catheter 32 and/or the embryo transfer catheter 28, and/or the FIG. 2B illustrates that the delivery catheter 32 distal end can have an everting balloon 22 that can be in a fully everted configuration. The everting balloon system 8 can be equipped with a distal end opening or a pre-determined valve.

FIG. 2C illustrates the embryo transfer catheter distal end 36 can extend beyond the distal end of the fully everted everting balloon membrane 6. The everting catheter system 106 can access a bodily cavity (e.g., the uterine cavity or fallopian tubes) to deliver or introduce tools (e.g., instruments), reproductive media or material (e.g., embryos, in vitro fertilization (IVF) or insemination products, such as hormones), contrast media, dye, therapeutic agents, sclerosing agents to treat the endometrium, insufflation media, or combinations thereof to the cavity. For example, reproductive media can be delivered with a transfer catheter inserted through the inner catheter lumen 12 to the uterine cavity.

FIG. 2B illustrates that a transfer catheter or insemination catheter can have a transfer connector 34, such as a female luer connector, a strain relief length, and a transfer tube. The transfer tube can hold the reproductive media. A delivery force, for example a positive fluid pressure, can be delivered through the transfer connector 34 and strain relief length to push the contents of the transfer tube into the target site.

The transfer catheter can attach to or inserted through the inlet port. The transfer tube can hold an embryo, for example for in vitro fertilization or IVF. The embryo transfer catheter 28 can deliver embryos through the system and to the uterine cavity and other agents that help facilitate embryo implantation such as materials that promote adherence of the embryo to the uterine endometrium. The embryo transfer catheter 28 can have a distal end configuration that can promote implantation of the embryo(s) within the endometrial wall or within the sub-endometrial surface.

The embryo transfer catheter 28 can hold spermatozoa and deliver the spermatozoa through the system and to the uterine cavity for intrauterine insemination procedures. The transfer catheter can hold and deliver or deposit materials, such as drugs, therapeutic agents, instruments, endoscopes, cytology brushes, other catheters, or combinations thereof through the system and into the uterine cavity. The transfer catheter can be connected to a vacuum source for the aspiration of materials from the uterine cavity or other bodily cavities and lumens.

The transfer catheter and/or materials can be loaded in the inner catheter lumen 12 prior to everting the everting balloon 22 within the vessel or bodily cavity. For example in the case of delivery of reproductive material in the uterine cavity, the transfer catheter can be loaded with washed and prepared semen in the transfer tube and the transfer catheter can be placed in the inner catheter lumen 12.

The inner catheter 10 can be extended and the everting balloon 22 can evert and unroll through the cervix and into the uterine cavity. Concurrently or subsequently, the transfer catheter can be advanced through the inner catheter lumen 12 into the uterine cavity. Once fully everted or when the transfer catheter becomes extended or exposed from the inner catheter 10 and beyond the everting balloon membrane 6, the reproductive material in the transfer catheter can be deposited by a syringe 66, squeeze bulb, piston, or other pressure system. A second delivery catheter 32, such as a second insemination, IVF, or drug delivery catheter 32 can be concurrently inserted into the inlet port or a second inlet port. The second delivery catheter 32 can be deployed to the target site concurrent with or subsequent to the transfer catheter. The embryo transfer catheter 28 can advance distally within the everting balloon 22 and the inner catheter lumen 12. The transfer catheter can deposit the reproductive material (e.g., sperm) within the uterine cavity.

Figure 3A:
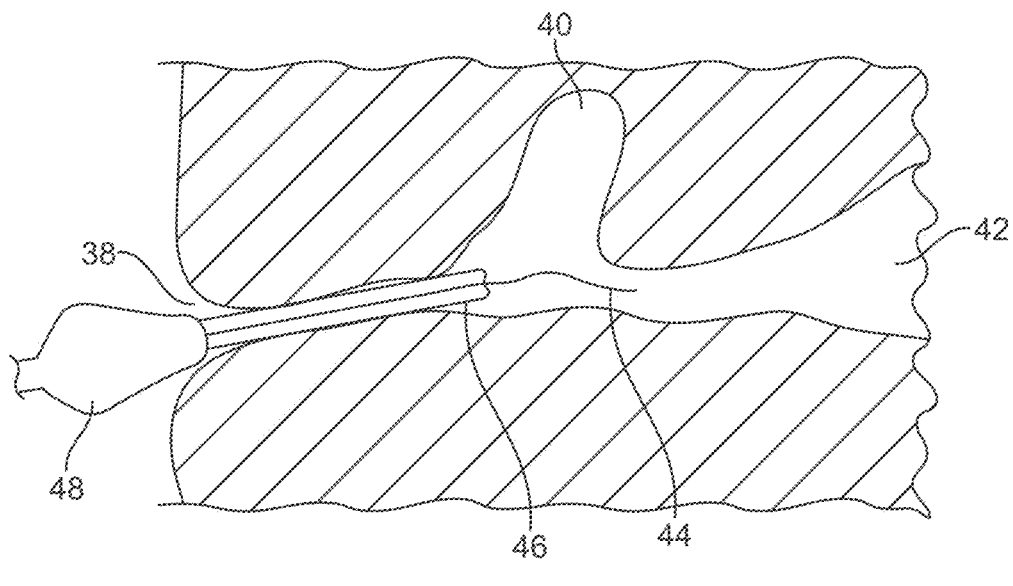
FIG. 3A illustrates a cross-sectional view of a flexible tip guidance wire beyond the distal end of the everting balloon membrane during the eversion process directing the everting balloon system beyond a cul-de-sac in the endocervical canal.

FIG. 3A illustrates a cross-sectional view of a flexible tip guidance wire 44 extending beyond the distal terminal end of the everting balloon membrane 6 during the eversion process directing the everting balloon system 8 beyond an endocervical canal cul-de-sac 40. The distal end of the delivery catheter 112, for example the delivery catheter acorn tip 48, can be seated against or near the cervical entrance 38. The flexible tip guidance wire 44 can be advanced beyond the opening of the cul-de-sac 40 and can be positioned within the cervical entrance 38 or opening towards or within the uterine cavity entrance 42. The delivery catheter 32 system can be equipped with a flexible tip guidance wire 44 that allows the physician to steer or direct the leading edge of the everting balloon 22 to the correct path within the uterus, for example, to facilitate access within the uterine cavity entrance 42 and through the cervical canal.

The delivery catheter 32 system can be used, for example, when a defect, such as a C-section defect or scar, cul-de-sac 40, or crypt is present within the endocervix. Such defects can be visualized before, during or after delivery of the flexible tip guidance wire 44, via transabdominal or transvaginal ultrasound. The echogenicity of the delivery catheter 32 is enhanced by pressurization fluid, or air, or a combination of both that creates echogenic density differences that are visualized by ultrasound. The flexible tip guidance wire 44 can be introduced beyond the cul-de-sac 40 opening and towards the uterine cavity or target site, for example, to avoid the defect or cul-de-sac 40. The internal balloon pressure can be reduced or eliminated, for example, to advance the flexible tip guidance wire 44 beyond the everting balloon distal end 46. With everting balloon pressure low or at zero, the flexible tip guidance wire 44 can be threaded through the deflated balloon membrane 6 and advanced beyond the cul-de-sac 40 opening. Once the flexible tip guidance wire 44 is advanced beyond the opening and towards the target site, the everting balloon membrane 6 pressure can be re-established and the advancement of the inner catheter 10 can continue until the everting balloon distal end or leading end moves past or distal to the cul-de-sac 40 opening.

Figure 3B:
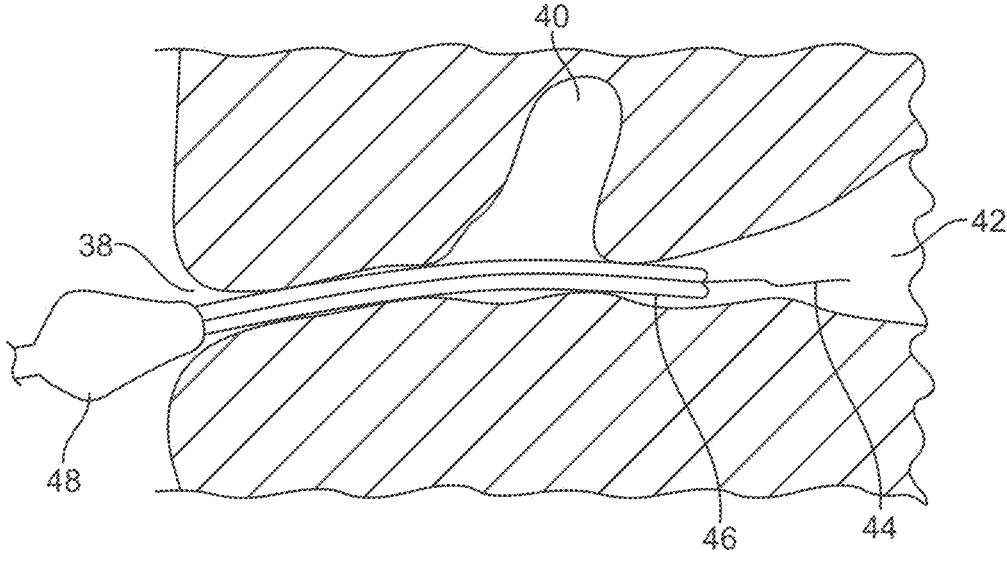
FIG. 3B illustrates a cross-sectional view of a flexible tip guidance wire beyond the distal end of the everting balloon membrane at the completion of the eversion process beyond a cul-de-sac in the endocervical canal.

FIG. 3B illustrates a cross-sectional view of a flexible tip guidance wire 44 beyond the distal end of the everting balloon membrane 6 at the completion of the eversion process beyond a cul-de-sac 40 in the endocervical canal. In this view, the everting balloon system 8 has been advanced towards and within the uterine cavity without entering the cul-de-sac 40. Once past the opening and towards the uterine cavity or target location, the flexible tip guidance wire 44 can be removed once full eversion is complete, or prior to that by reflating the everting balloon 22 pressure to allow removal of the flexible tip guidance wire 44.

Figure 4:
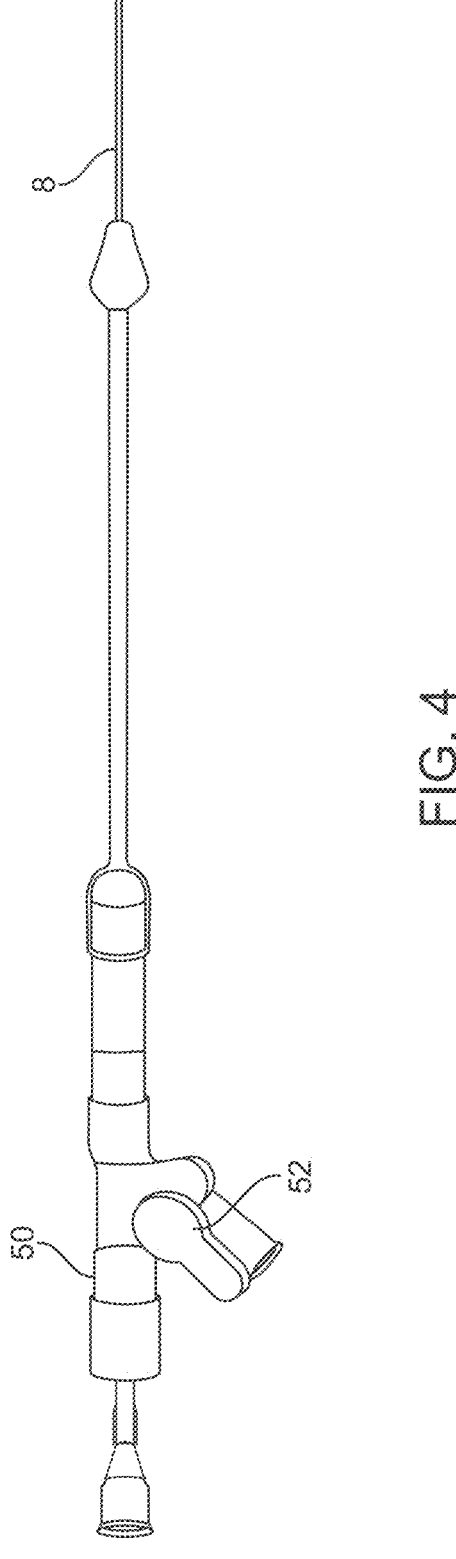
FIG. 4 illustrates a variation of the everting balloon system with an alternative stopcock configuration for maintaining pressurization.

FIG. 4 illustrates a variation of the everting balloon system 8 in a fully everted configuration and with a stopcock 52, for example, for maintaining pressurization. The stopcock 52 can be attached to or placed on the Y-fitting 50 connector which can be used by the physician to hold the everting balloon system 8 during the procedure. The location of the stopcock 52 lateral to the body of the catheter can allow finger-tip control of the pressurization state of the everting balloon system 8 by manipulating the stopcock 52 orientation with the physician's fingers. At the completion of the eversion for the inner catheter 10, the pressurization state of the everting balloon membrane 6 can be quickly removed. The removal of the pressurization state can occur prior to, during, or after the insertion of the embryo transfer catheter 28. Alternatively, the removal of the pressurization state can occur prior to, during, or after the deposition of the embryo (s) from the embryo transfer catheter 28. Yet further, the removal of the pressurization state can occur prior to, during, or after the removal of the embryo transfer catheter 28. Once the pressurization state is removed from the everting balloon system 8 and after the embryo(s) have been deposited within the uterine cavity, the entire everting balloon system 8 can be withdrawn from the uterine cavity.

Figures 5A, 5B:
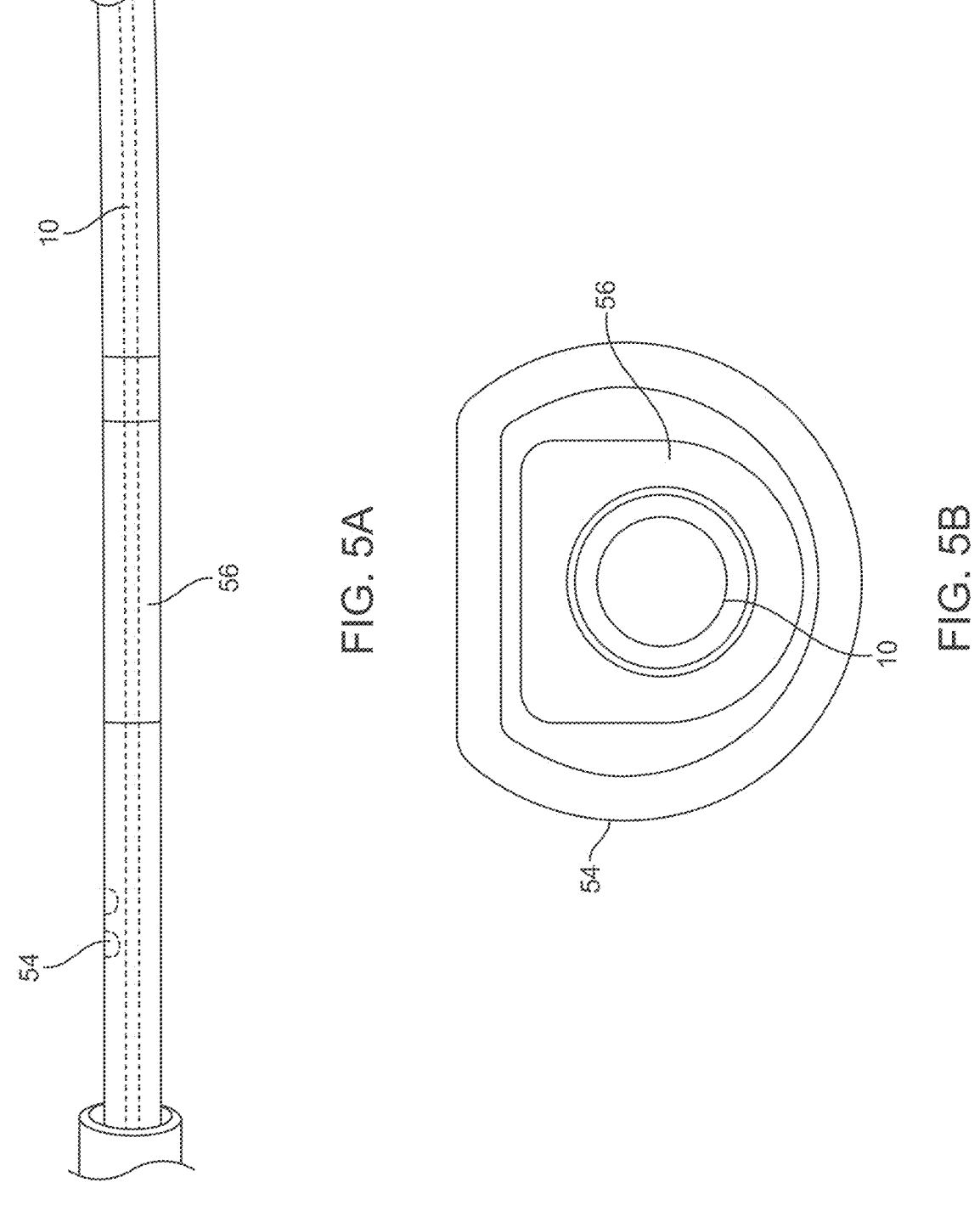
FIG. 5A illustrates a variation of the everting balloon system with an internal alignment mechanism that prevents rotation and spinning of the balloon membrane.
FIG. 5B illustrates a cross-sectional axial view of the internal alignment mechanism and mating geometry of the delivery catheter tubing.

FIG. 5A illustrates a variation of the everting balloon system 8 with an internal alignment mechanism 56 that can prevent or minimize rotation and spinning of the balloon membrane 6. The twisting of the balloon system can be restricted or eliminated. Multiple twists within the balloon system can, for example, hinder the advancement of the embryo transfer catheter 28 or other instruments and tools through the everting balloon system 8. An internal alignment mechanism 56 of alignment piece can be located within the outer tubing 54 distal to the Y-fitting 50 and stasis valve that can maintain pressurization within the everting balloon system 8 while the inner catheter 10 within the delivery catheter 32 is being advanced or retracted during the eversion process.

FIG. 5B illustrates a cross-sectional axial view of the internal alignment mechanism 56 and mating geometry of the delivery catheter 32 tubing. The inner surface of the outer tubing 54 of the delivery catheter 32 can have a D-shaped configuration. The alignment piece on the inner catheter 10 can be keyed within the D-shape of the outer tubing 54, for example, to restrict or eliminate the rotation of the inner catheter 10 in relation to the outer tubing 54. The alignment piece can be made from a material with a lubricous coating, Teflon, or other material that reduces the friction of the alignment piece when being moved in the outer tubing 54.

The D-shape can alternatively be an oval or elliptical shape, with a mating oval or elliptical shape on the alignment piece that restricts or eliminates the rotation of the inner catheter 10 in relation to the outer tubing 54.

Alternatively, the alignment piece shape can be configured as the external surface throughout the entire inner catheter 10 tubing body. The shape of the external surface would in this configuration mate with the internal geometry of the outer tubing 54. The surfaces can "key" into each or interference fit against each other, for example, to restrict or eliminate the rotation of the inner catheter 10 to the outer tubing 54 and the stasis valve would need to conform or fit to the external surface of the inner catheter 10 to maintain pressurization during the eversion process. As an example, the inner catheter 10 tubing can be configured with a rail surface or protrusion that mates or "keys" with receptacle within the outer tubing 54 internal geometry.

Figure 5C:
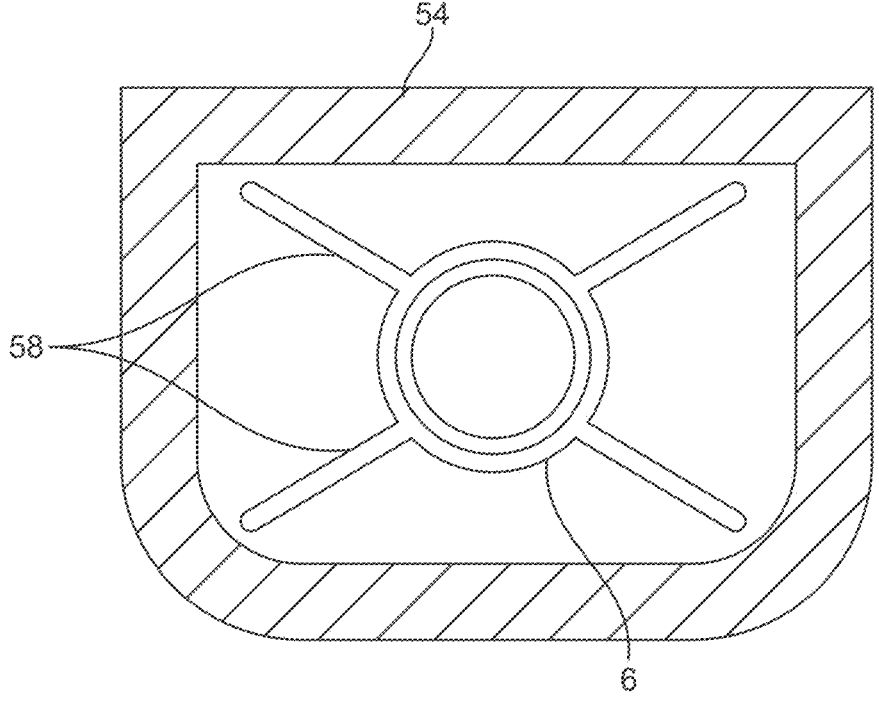
FIG. 5C illustrates another embodiment of the alignment piece.

FIG. 5C illustrates that the alignment piece can have splines 58 extending radially outward from the inner catheter 10. The splines 58 can abut or mate within the internal geometry of the outer tubing 54. The spline outer surfaces can engage the internal geometry of the outer tubing 54, for example, to restrict or eliminate the rotation of the inner catheter 10 in relation to the outer tubing 54. The spline surfaces can have minimal edges or corners that can have a reduced surface area contacting the internal walls of the outer tubing 54. The reduction of surface area can reduce the friction of the alignment piece when moved within the outer tubing 54.

Figure 6:
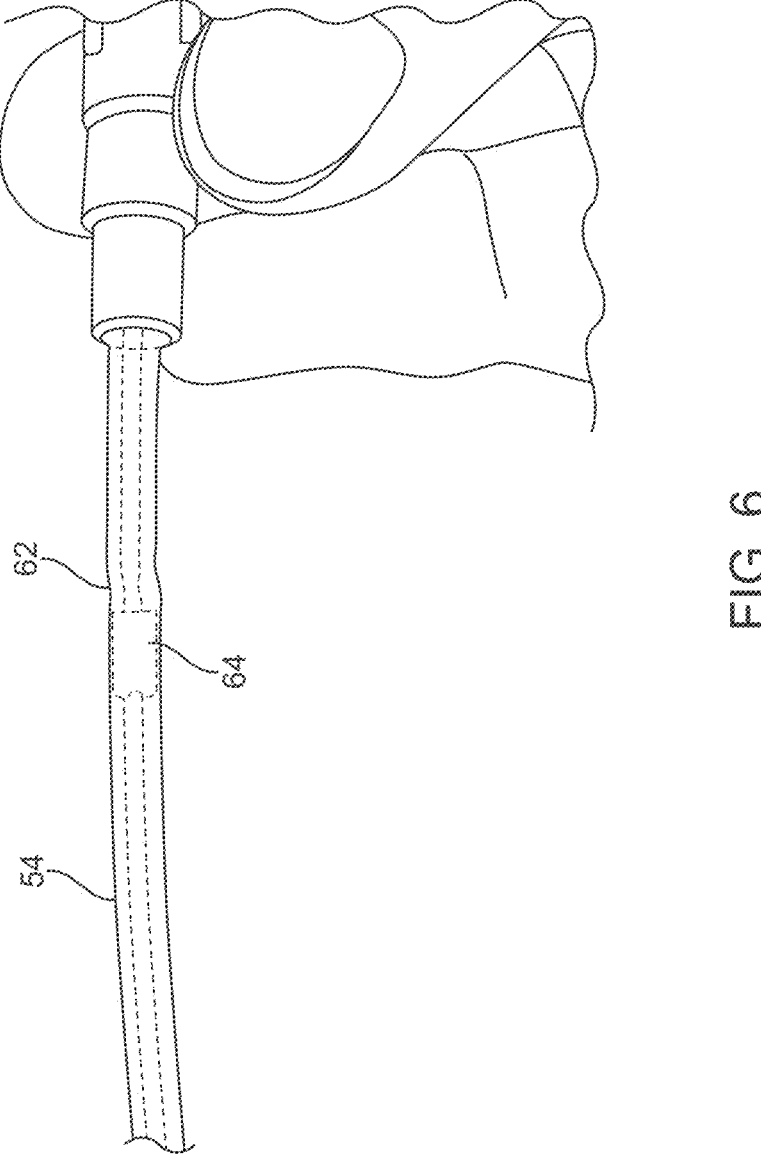
FIG. 6 illustrates a variation of an everting balloon system with an internal mechanism that prevents over-elongation of the inner catheter during balloon inversion.

FIG. 6 illustrates that the everting balloon system 8 can have an internal mechanism stopper 64. The outer tubing 54 of the delivery catheter 32 can have a crimp 62. The internal mechanism stopper 64 can prevent or minimize over-elongation of the inner catheter 10 during balloon inversion by abutting or interference fitting against the crimp 62. In use during the eversion and inversion procedure, or during the preparation of the everting balloon system 8, the end user or physician can inadvertently retract the everting balloon system 8 and over-extend the balloon membrane 6. The over-extension can stretch, weaken, or damage the balloon membrane 6. Visual indicators or markings are useful but may not prevent over-extension if the end user is not diligent or is within a setting in which the indicia is readily visual. The stopper 64 is located on the inner catheter 10 tubing body and is positioned at point where full inversion has occurred. At full inversion, the stopper 64 contacts a mechanical detent, crimp 62, stop, or the distal end of the Y-fitting 50 connection, and prevents further retraction of the inner catheter 10 thereby eliminating the over-extension of the balloon membrane 6 beyond the full inversion state. The stopper 64 could mechanically contact other mechanical structures built into the outer tubing 54 such as a crimp 62 as shown in FIG. 6, or a reduction in internal diameter of the outer tubing 54, in which the stopper 64 would engage the crimp 62 or reduction in internal diameter of the outer tubing 54 to physically prevent further retraction of the inner catheter 10 beyond the full inversion state.

Figure 7A:
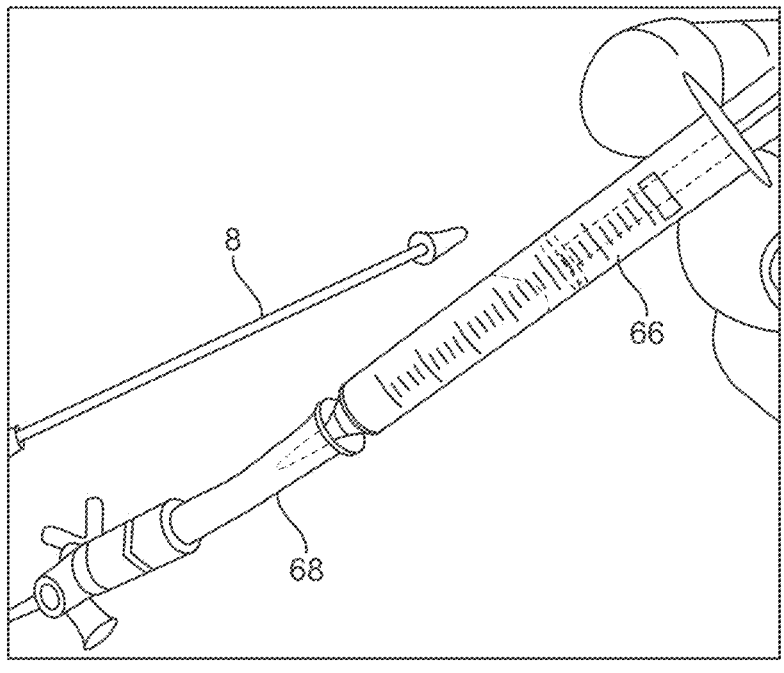
FIGS. 7A, 7B and 7C illustrate everting balloon systems with a compliant pressurization apparatus that's provides a pre-determined pressure within the catheter system with an indicator to the user that system is at the appropriate operating pressure.
Figure 7B:
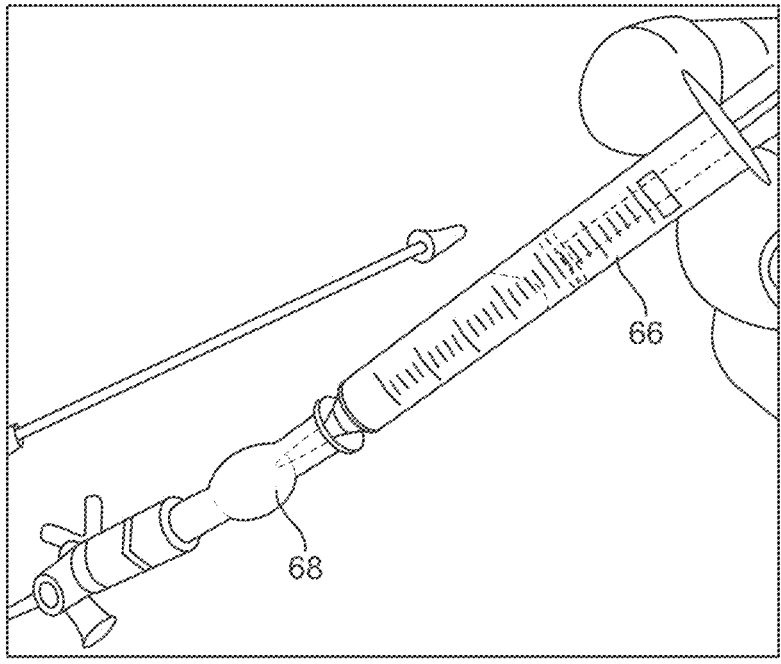
Figure 7C:
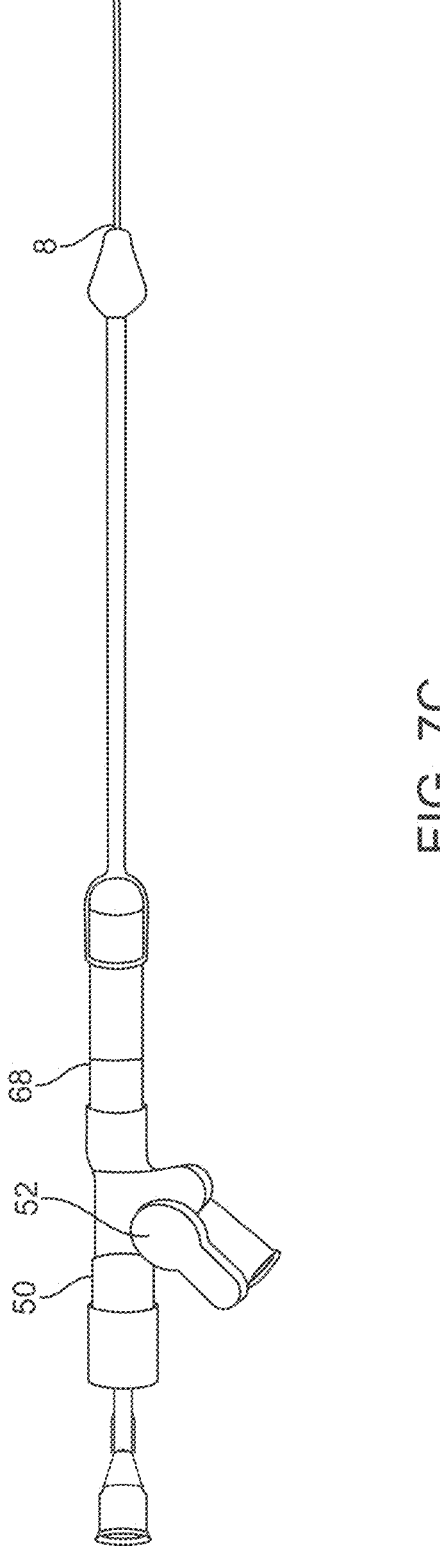

FIGS. 7A, 7B and 7C illustrate that the everting balloon systems 8 can have a compliant pressurization apparatus or element that can provide a pre-determined pressure within the catheter system with an indicator to the user that the system is at the appropriate operating pressure.

FIG. 7A illustrates that a compliant member 68 can be in the everting balloon system 8. The compliant member 68 can be configured as a separate component or accessory to assist the end user in preparing the everting balloon system 8. As the pressurization of the everting balloon system 8 occurs, for example as fluid 70 is pressed from the syringe 66 into the everting balloon system 8, the compliant member 68 can inflate. The inflation of the compliant member 68 can be a visual indicator that the system contains pressure. The compliant member 68 can be made from silicone tubing or balloon, other elastomeric materials such as polyurethane, rubber, latex, or combinations thereof. The compliant member 68 can be configured as one or more tubing or balloons.

FIG. 7B illustrates that the compliant member 68 can expand radially and lengthwise upon the influence of instilled fluid media from the syringe 66. The expansion of the tubing walls of the compliant member 68 can act to dampen the fluid pressure within the everting balloon system 8. This can allow for variance in the amount of fluid 70 instilled by the end user that could impact the pressure rise in the everting balloon system 8. The amount of air in the everting balloon 22 also provides some compliance to the everting balloon system 8 and hence the complaint member can provide a range of fluid volumes without exceeding the recommended working pressure of the everting catheter system 106.

As a representative example, one embodiment of the everting catheter system 106 can operate in a pressure range from about 2 to about 4 atmospheres of pressure with a nominal pressure of about 3 atmospheres. For advancement within the cervical canal and into the uterine cavity, any residual air within the everting balloon system 8 can be removed before, during and/or after the eversion process. This can be particularly advantageous in situations with tight or stenotic cervices. One method to achieve a working pressure of 3 atmospheres is to connect a pressure gauge to the everting balloon system 8. In practice pressure gauges and inflation devices are expensive to the overall cost of the system. Another method to achieve a working pressure of 3 atmospheres is to prescribe an exact fluid volume amount to the everting balloon system 8 that must be instilled by the end user prior to use. In practice this can accomplish a working pressure of 3 atmospheres but requires diligence by the end user to both fluid volumes and the amount of air in the everting balloon system 8. The attachment of the compliant member 68 to the everting balloon system 8 can accomplish consistent fluid pressures within a wider range of fluid volumes that provides a larger tolerance to end user diligence during the catheter preparation process. This is demonstrated with a compliant member 68 attached to an everting balloon system 8 with a recommended fill volume of 3 cc of fluid 70. For test purposes while measuring preparing the everting catheter system 106 with varying amounts of fluid volume, the internal pressure of the system does not alter (much) beyond the nominal pressure of 3 atmospheres and in all fluid volumes, even when the fluid volume is intentionally doubled beyond the instructed amount, the internal pressure of the everting balloon system 8 can remain within the operating working range of the system. For this test, the complaint member is constructed with 50 durometer silicone tubing with a 0.250" ID and a 0.500" OD and a 1.5 cm length of silicone tubing. At the ends of the compliant member 68 (e.g., silicone tubing) can be male and female luer connectors with attachment rings to mechanically adhere the silicone tubing to the luer connectors. As the silicone tubing is filled with fluid 70, the radial walls can expand and the overall length of the silicone tubing can increase in response to the increasing volume of fluid 70. The internal fluid pressure of the everting balloon member can plateau at or near the desired nominal pressure amount, for example since the additional fluid volume is accommodated by the compliant member.

| Fluid Volume Within Everting Balloon System and Complaint Member | Resultant Internal Pressure Within the Everting Balloon System |
| --- | --- |
| 3 cc of saline | 3.0 atmospheres |
| 4 cc of saline | 3.0 atmospheres |
| 5 cc of saline | 3.2 atmospheres |
| 6 cc of saline | 3.3 atmospheres |

As seen in the above exemplary data table, the resultant internal pressure can remain within the specification range from about 2 to about 4 atmospheres and at or near the nominal pressure of 3 atmospheres. In this set of experiments and with this configuration of the complaint member, a fluid volume of about 2× the amount yielded a 10% increase in internal pressure. By altering the durometer, elastomeric properties, length and wall thickness of the compliant, other nominal pressure amounts can be obtained. One of the additional benefits of the compliant member 68 is that it provides a safety margin against over-pressurization that can either damage the balloon system, or provide an everting balloon system 8 that operates outside of its operational working parameters. The complaint member can be used in combination with a pressure relief valve in everting balloon systems 8 that have more critical or tight pressure tolerances, or where internal pressure changes due to operator or anatomical factors can create internal pressures that go beyond the normally-expected performance specification.

FIG. 7C illustrates that the compliant member 68 can be located on the outer tubing 54 of the everting balloon system 8. The location of the compliant member 68 can be a visual indicator to the physician on the pressurization state of the everting balloon system 8 and can impact the internal pressure of the everting balloon system 8 due to its compliance properties. The complaint member can be made from elastomeric materials such as silicone, polyurethane, PVC, rubber, latex, or combinations thereof. The compliant member 68 can be shaped as a tube or a preformed balloon.

The entire compliant member 68 can be held by the physician during use. The entire complaint member can be grasped and squeezed while maintaining positional control of the everting balloon system 8.

Squeezing (i.e., applying external mechanical pressure) the complaint member circumferentially can create small rises in the internal pressure of the everting balloon system

8 that can advance the everting balloon 22 through tight or narrow anatomical passages. Relaxing the grasp (i.e., external mechanical pressure) on the complaint member would instantly return the complaint member and the everting balloon system 8 to the pervious operating pressure range. The complaint member can be pulsed or vibrated (e.g., with external mechanical pressure), for example, providing pulsatile fluid pressure spikes within the everting balloon system 8, for example for advancement through tight or narrow passageways and/or advancement of the everting balloon 22 in small and discrete steps, and/or with minor increases in internal pressure.

Figure 8:
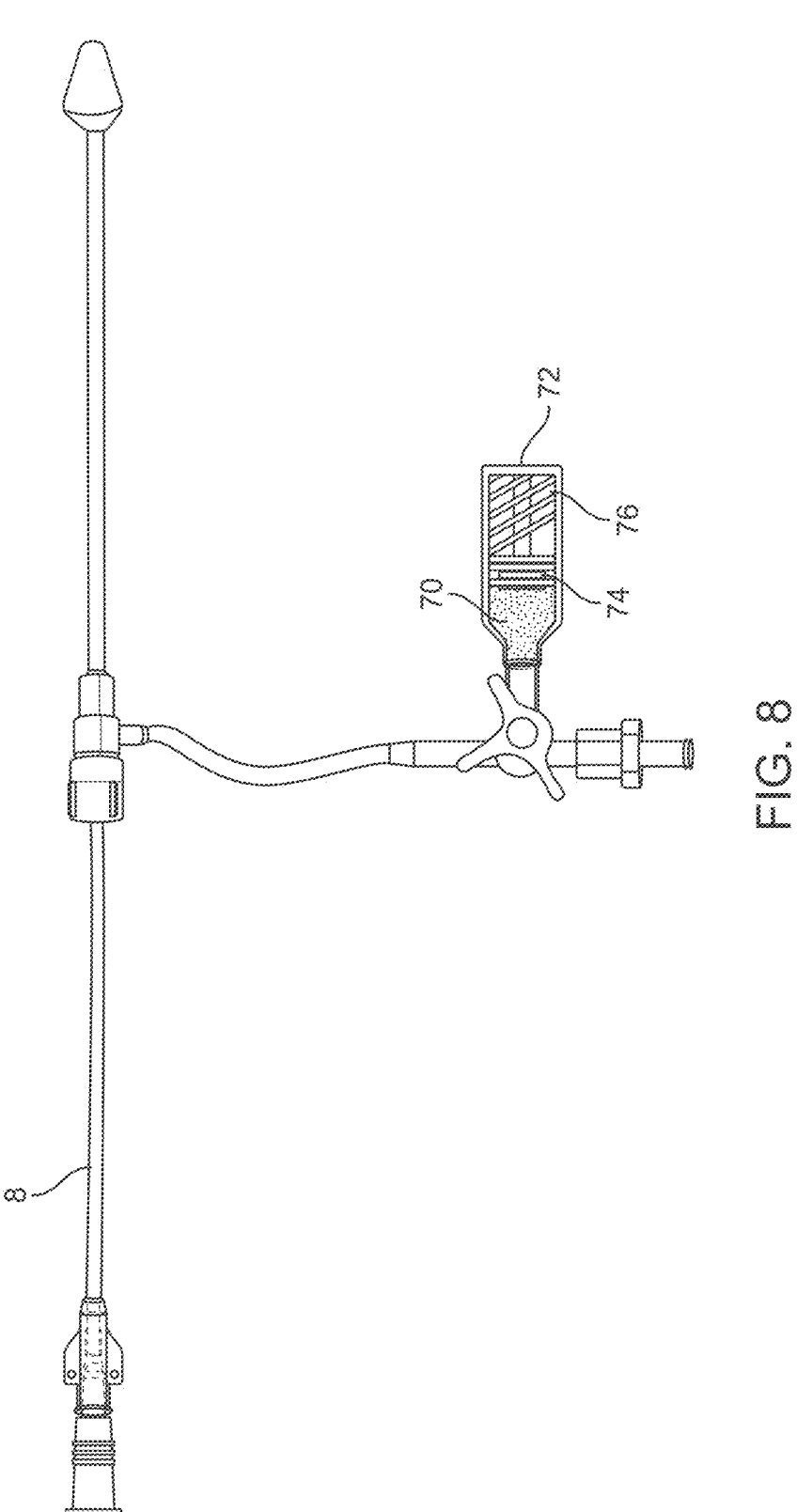
FIG. 8 illustrates another embodiment of an everting balloon system with a mechanism that automatically pressurizes the everting balloon system to a predetermined amount.

FIG. 8 illustrates that the everting balloon system 8 can have a mechanism that automatically pressurizes the everting balloon system 8 to a predetermined amount. In a side view, a rigid compliance canister 72 that has a syringe plunger 74 and spring assembly 76 can be attached to or configured onto the everting balloon system 8. The chamber can have a fluid reservoir 82 filled with a fluid 70 in communication with the internal volume of the everting balloon system 8 and in contact with the syringe plunger 74. The fluid 70 can supply internal pressure to the everting balloon 22. The syringe plunger 74 and spring assembly 76 can have a spring 150 that can drive the plunger into the chamber with a known spring 150 constant or K factor. The spring 150 can deliver a predetermined internal pressure to the everting balloon system 8. The spring 150 can provide fluid 70 or pressure compliance to the everting balloon system 8 to maintain the internal pressure within the operating range and the spring 150, like the complaint member, can be responsive to changes in fluid volume, the everting balloon system 8 itself as it everts and inverts, and any anatomical forces acting on the everting balloon system 8.

The everting balloon system 8 can have a syringe plunger 74 and air pressure canister 72 (e.g., in combination with or in place or the syringe plunger 74 and spring assembly 76 shown in FIG. 8) in which the air canister 72 has a predetermined internal gas pressure (e.g., providing fluid compliance like the spring assembly 76). Pressure from the air canister 72 acting on the plunger can drive the fluid volume within the everting balloon system 8 to a predetermined internal pressure range. The air pressure canister 72 can be prefilled with $CO_2$ gas, air, or other gas.

Figure 9A:
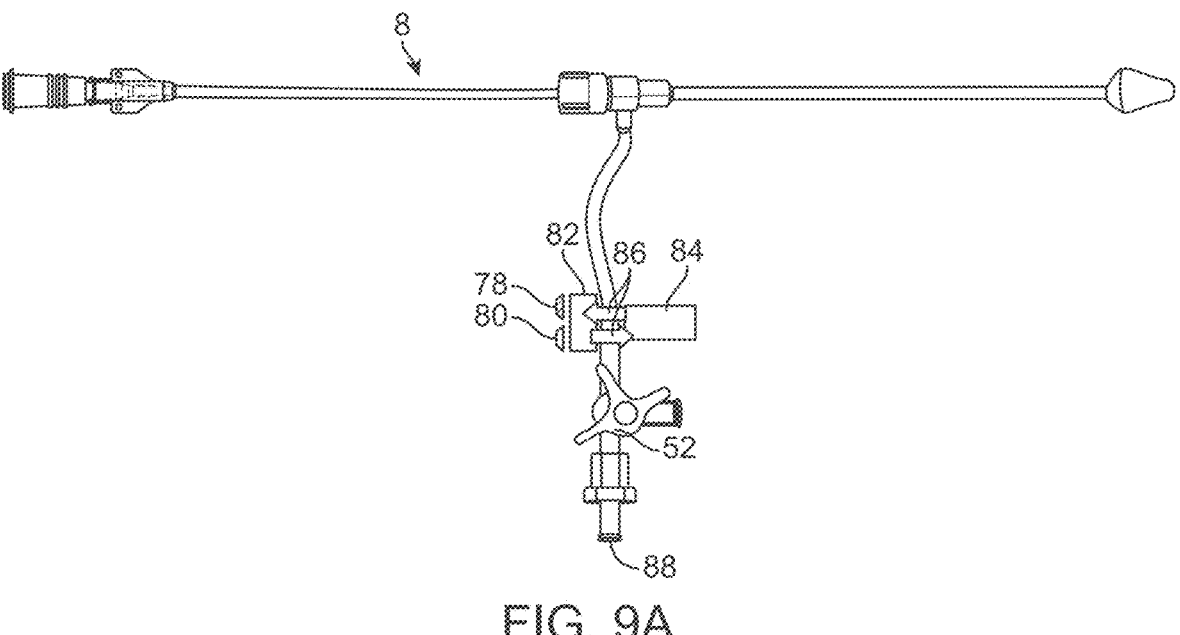
FIG. 9A illustrates an everting balloon system with an integral pressurization system that provides an indicator and the ability to quickly shift the pressurization state of the balloon system from pressurized to non-pressurized at the fully everted state of the everting balloon system.

FIG. 9A illustrates that the everting balloon system 8 can have an integral pressurization system 88 that can provide an indicator and the ability to quickly shift the pressurization state of the balloon system from pressurized to non-pressurized at the fully everted state of the everting balloon system 8 via actuating slide or trumpet valves for fluid 70 from a constant pressure source 84 to a separate fluid reservoir 82. Actuation of trumpet valves directs fluid 70 back into the constant pressure source 84 through one-way valves 86. The one-way valves 86 can be part of the trumpet valves. A stopcock 52 is used to prepare and fill the everting balloon system 8 with fluid 70. For example, a first trumpet valve 78 an release fluid 70 into the fluid reservoir 82, and a second trumpet valve 80 can return to the constant pressure source 84.

Figure 9B:
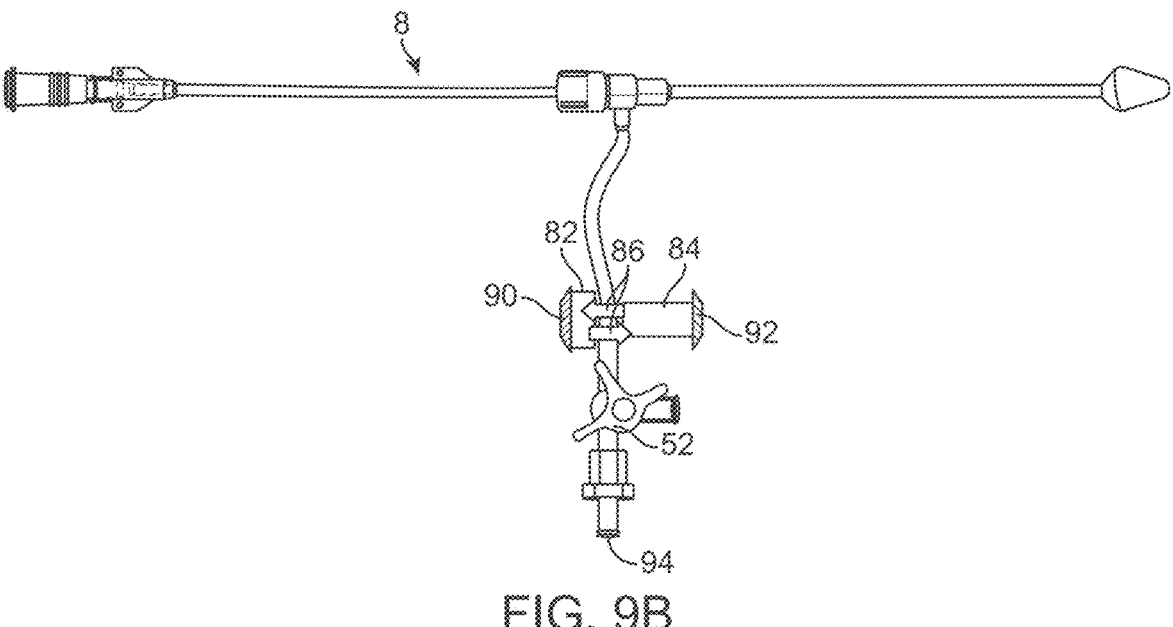
FIG. 9B illustrates an everting balloon system with an integral pressurization system that provides an indicator and the ability to quickly shift the pressurization state of the balloon system from high pressurization to low pressurization, and back to high pressurization, or multiple intermediate states of pressurization, during the eversion process.

FIG. 9B illustrates an everting balloon system 8 with an integral pressurization system that provides an indicator and the ability to quickly shift the pressurization state of the balloon system from high pressurization to low pressurization, and back to high pressurization, or multiple intermediate states of pressurization, during the eversion process. A switch valve diverter and diaphragm 90 on the fluid reservoir 82 can open and close the fluid pathway into the everting balloon system 8 from the constant pressure source 84 and fluid reservoir 82. Depressing the plunger or diaphragm 90 of the fluid reservoir 82 returns the fluid volume back into the everting balloon system 8 and in communication with the constant pressure source 84. While fluid 70 is diverted into the fluid reservoir 82, the internal pressure within the everting balloon system 8 drops to, or at, nears zero atmospheres. Depressing diaphragm 90 plunger of the fluid reservoir 82 pushes fluid 70 through one-way valve 86 into the constant pressure source 84 chamber. Manual depression forces on the diaphragm 90 are facilitated by the flexure of the diaphragm 90 surface from a convex profile to a concave profile as the fluid is pushed through the one-way valve 86 and into the constant pressure force chamber. Fluid 70 going into the constant pressure force chamber flows through a one-way valve 86 to enter the chamber. Once the diverter is flipped back to the everting balloon system 8, the constant pressure source 84 will instill the fluid 70 back into the everting balloon 22. Other combinations of one-way valves 86, check valves, or turn valves are possible to allow fluid pressure in the everting balloon systems 8 to change from an operating pressure state or a zero pressure state quickly without having to reconnect to the everting catheter 218 to a separately supplied fluid source, or without moving the position of the everting catheter 218 within the bodily cavity.

As another embodiment, the constant pressure source 84 could be configured to supply varying amounts of force for providing the internal pressure of the everting catheter system 106. The constant pressure source 84 can be supplied with a constant pressure regulator 92 that can modulate the amount of internal pressure being supplied to the everting balloon system 8. Pressure modulation can provide change from 3 atmospheres of pressure to 2, 1, or 0.5 atmospheres of pressure which can still provide the everting balloon 22 with structural shape but reduces the amount of eversion force, or the overall diameter of the everting balloon 22. In practice, as an example, the everting balloon 22 may have its internal pressure modulated from 3 atmospheres of pressure at a point of nearly complete eversion but would then have the internal pressure modulated to 0.5 or 1 atmospheres of pressure as the embryo transfer catheter 28 is being loaded by the embryologist, or when the embryo transfer catheter 28 is being traversed through the inner catheter 10, or at as the entire everting catheter 218 is inverted or removed from the uterine cavity without inverting the balloon back into the delivery catheter 32. Other degrees of pressure are possible with fingertip control of the physician without having to use an inflation device hooked up to the everting catheter system 106.

The everting balloon system 8 can have a fill port 94, for example to fill and/or empty the everting balloon system 8 (e.g., the everting balloon 22, constant pressure source 84, fluid reservoir 82, catheter inner volumes, connector inner volumes, or combinations thereof) with fluid 70.

Figure 10:
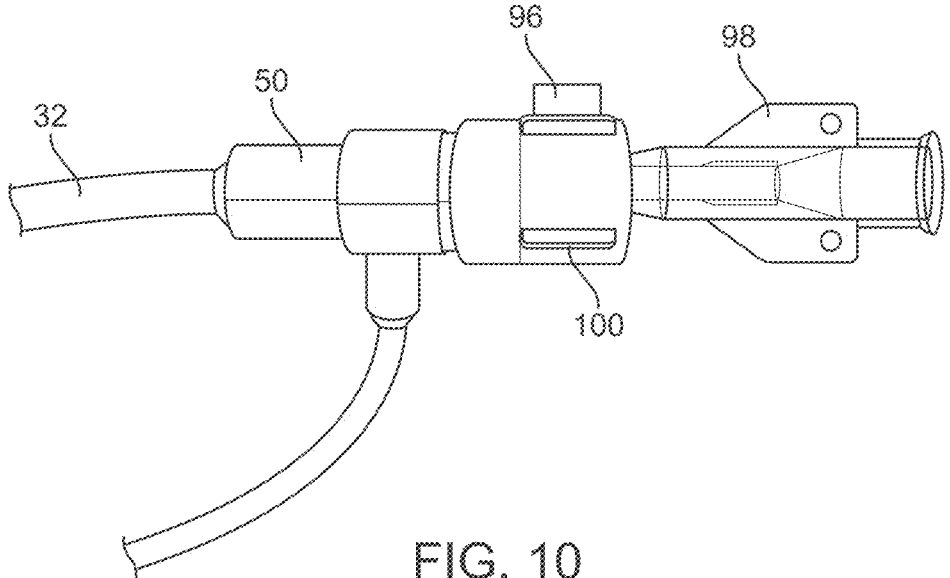
FIG. 10 illustrates an everting balloon system with a mechanism that stabilizes the inner catheter at the full eversion stage and provides an indicator to the user that catheter system is at the appropriate step in the process for embryo transfer.

FIG. 10 illustrates an everting balloon system 8 with a mechanism that stabilizes the inner catheter 10 at the full eversion stage and provides an indicator to the user that catheter system is at the appropriate step in the process for embryo transfer. For this embodiment, the inner catheter 10 and the everting balloon 22 reach full eversion when the inner catheter proximal hub 98 contacts the Y-fitting cap 100 of the delivery catheter 32. Receptacle on Y-fitting cap 100 is configured to accept and mate with the distal surface of the proximal hub. Contact of the inner catheter proximal hub 98 to the cap of the Y-fitting 50 can elevate a pop-up locking tab as a visual indicator of the engaged position. Mating action can be an audible or palpable, or both, as the two surfaces engage and lock. For the embryo transfer procedure, when the two surfaces engage and lock, the embryologist can provide the embryo transfer catheter 28 for traversing through the inner catheter 10. Depression of the pop up locking tab 96 to unlock can free the inner catheter proximal hub 98 from the mating surface. The two surfaces can engage without locking, or engage with a mechanical or friction fit that can be overcome by slight retraction by the physician. The mating action of the two surfaces can mechanically open turn valve on the Y-fitting 50 to remove internal pressure within the everting balloon system 8 to reduce profile of the everting balloon 22, for example, once the full eversion process is completed.

Figure 11:
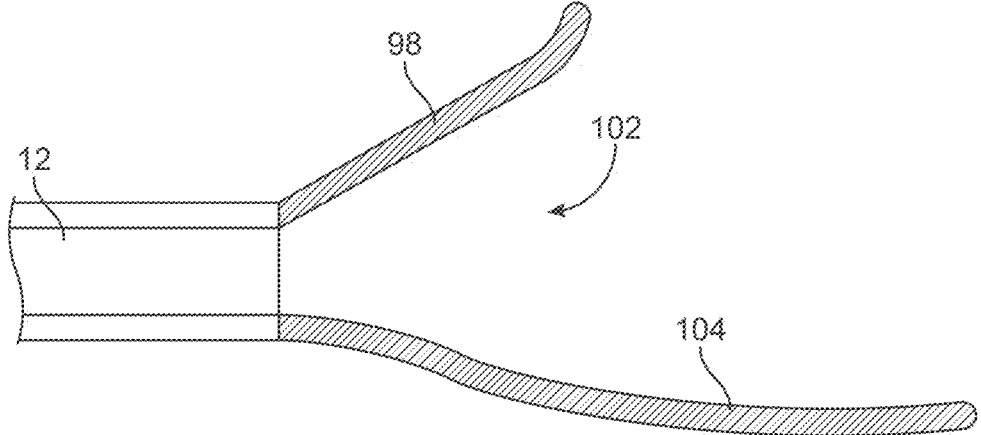
FIG. 11 illustrates an everting balloon system with a proximal hub connector that aids the physician and embryologist in delivering the embryo transfer catheter to the delivery catheter.

FIG. 11 illustrates in a side cross-sectional view an everting balloon system 8 with a proximal hub connector that can have a funnel, for example, for aiding the physician and embryologist in delivering the embryo transfer catheter 28 to the inner catheter lumen 12 of the delivery catheter 32. The inner catheter proximal hub 98 can have a large funnel opening 102, for example, to provide a target for the embryologist or the physician to place the distal end of the embryo transfer catheter 28 into the everting catheter system 106. The funnel of the proximal hub can also have a funnel posterior extension 104 that provides a platform for resting the proximal end of the embryo transfer catheter 28 during the final steps of embryo transfer catheter 28 insertion. This may be particularly beneficial with embryology syringes 66 that are heavy in weight, such as glass syringes 66, that could create extra downward forces on the embryo transfer catheter 28.

Figure 12A:
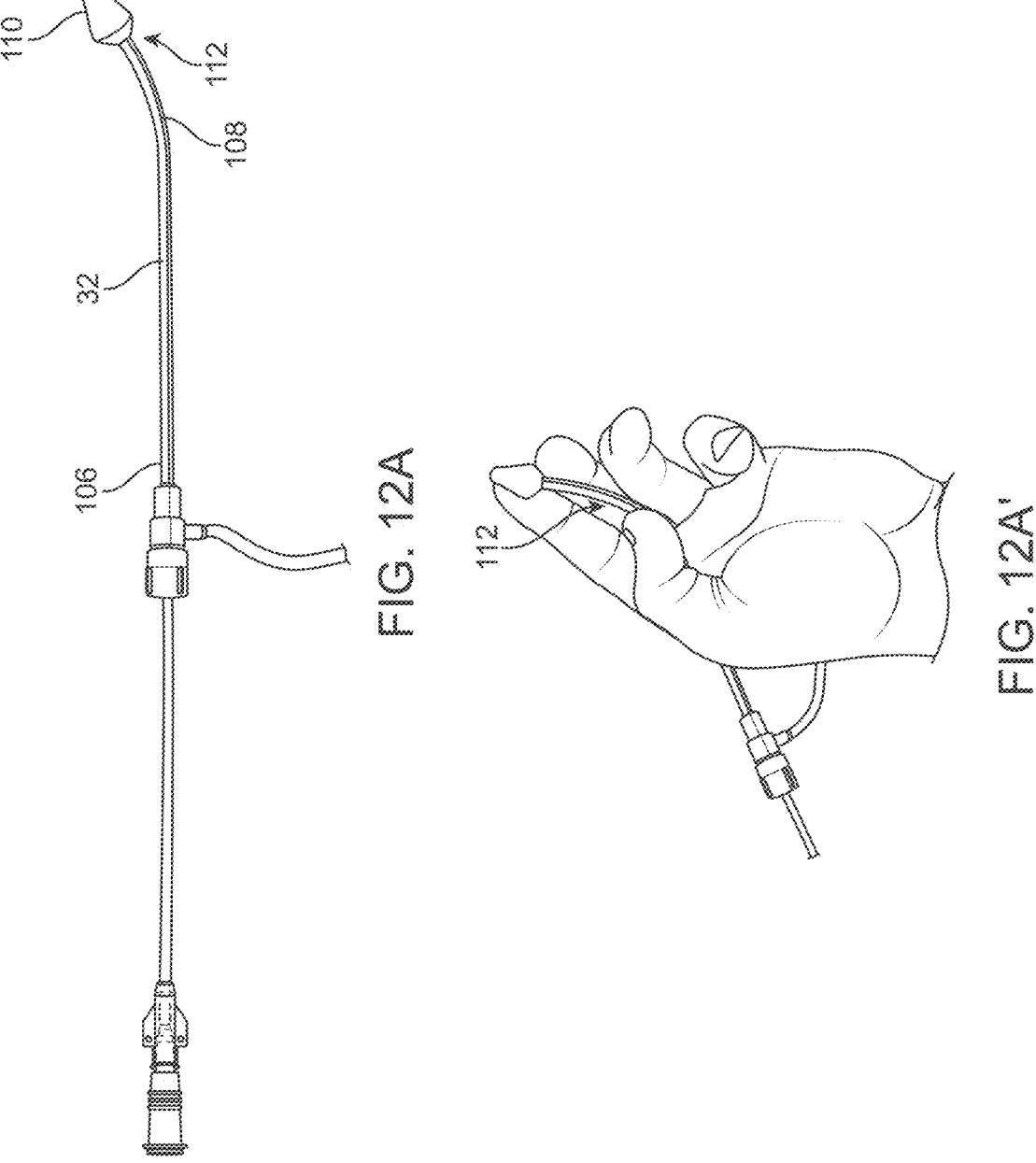
FIGS. 12A and 12A' illustrate a side view, and a perspective view while in the grasp of a hand, respectively, of an everting balloon system shaped with distal end features that facilitate uterine access without the need for a speculum.
Figure 12B:
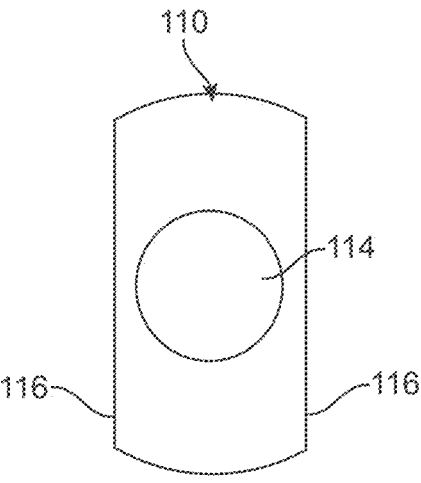
FIG. 12B illustrates in an end-on axial view of a variation of the acorn tip and distal end features that facilitate uterine access without the need for a speculum.

FIGS. 12A and 12A' illustrate a side view and a perspective view while in the grasp of a hand, respectively, of an everting balloon system 8 shaped with distal end features that facilitate uterine access without the need for a speculum. During embryo transfer procedures, minimizing the manipulations to the patient's uterus, cervix, and vagina is both more comfortable to the patient but can also have a significant role in reducing the amount of uterine contractions that could spontaneously arise during a procedure as a result or response to the manipulations. Uterine contractions can have a deleterious effect to the implantation of embryos during a procedure. The insertion of a speculum itself has been demonstrated to elicit uterine contractions and is uncomfortable to the patient. The embodiment of the everting catheter system 106 in FIGS. 12A and 12B also facilitates the use of a transvaginal ultrasound probe 198 during the embryo transfer procedure. Transvaginal ultrasound provides greater vision quality than an abdominal ultrasound in which the abdominal ultrasound probe needs to provide sound waves through the pelvic region of the patient which may have varying degrees of abdominal fat. Also abdominal ultrasound is enhanced by the patient having a full bladder which can also add to the discomfort to the procedure. The use of a transvaginal ultrasound probe 198 during an embryo transfer procedure is difficult since existing embryo transfer catheter 28 systems require a speculum for insertion of the device into the cervix. The embodiment illustrated in FIGS. 12A and 12B is designed to provide rigidity to enter into the vagina and press off the posterior surface of the vagina. Distal end angulation or curvature is designed to direct the distal tip of everting catheter 218 towards to cervical os.

FIG. 12B illustrates that the acorn tip 110 can be shaped for placement alongside the transvaginal ultrasound probe 198 by having flat surfaces 116 on either side of the acorn tip 110. The acorn tip 110 can have a distal end hole 114 or port. The physician can place the transvaginal probe into the vagina and alongside the cervix. The everting catheter system 106 can be introduced alongside the transvaginal probe until the acorn tip 110 is at the exocervix. The presence of the transvaginal ultrasound probe 198 would create access, and in most cases, room in the vagina for visual confirmation of placement at the exocervix without the need for a speculum. The everting balloon 22 would be then placed into the endocervical canal. For an everting catheter system 106, the portion of the everting catheter 218 that contacts the endocervix and uterine cavity is all contained within the delivery catheter 32 and does not contact the surfaces or fluids in the vagina, thus further obviating the need for a speculum during the procedure. As shown in FIG. 12A, the posterior side of delivery catheter 32 has a curved flexure support 108. Flexure support 108 is designed to maintain distal end curvature for entry into the vagina and placement of the distal acorn tip 110 at the exocervix. Flexure support 108 has rigidity to push slightly downward in the vagina to retract vaginal tissues away from the cervix 202. FIG. 12A' shows the curvature of the delivery catheter 32.

FIG. 12B illustrates that the distal end with flat surfaces 116 on both sides of the acorn tip 110 can facilitate placement along either side of the transvaginal ultrasound probe 198 regardless of the physician being right or left handed.

Figure 13:
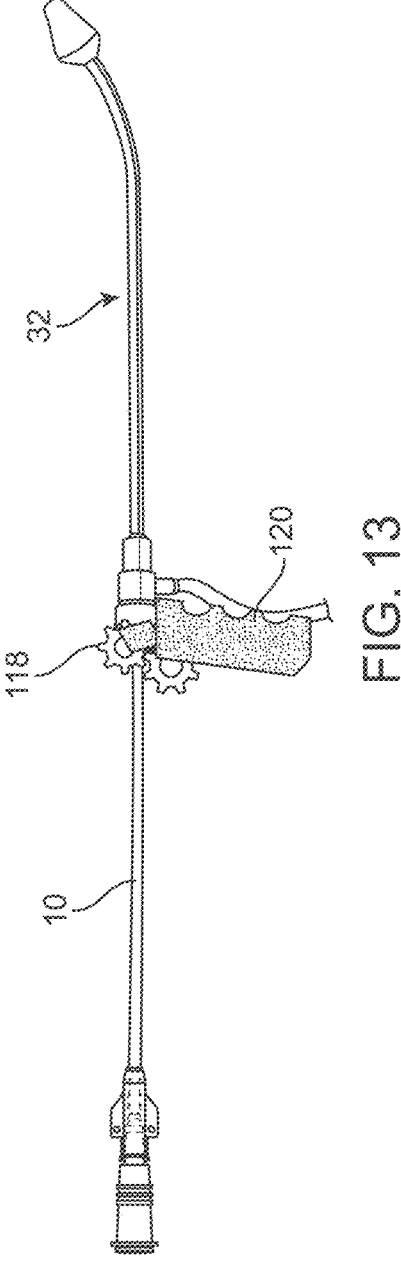
FIG. 13 illustrates in a side view of an everting balloon system with a handle that controls the translation of the inner catheter.

FIG. 13 illustrates in a side view of an everting balloon system 8 with a handle 120 and controller 118 that can control the translation 26 (e.g., advancing and retracting of) of the inner catheter 10. Handle 120 is designed to minimize the amount of overall working length of the everting catheter system 106 without adding length to the everting catheter system 106. As an example, working space needed to place a handle 120 within an everting catheter system 106 can increase the overall length to the delivery catheter 32, inner catheter 10, and the embryo transfer catheter 28 that needs to be placed within the system. Adding length to these systems can create handling issues within the embryology laboratory, especially in labs in which the loading of embryos within the embryo transfer catheter 28 is performed within a small incubator with side walls that will encroach on the handling of the embryology syringe 66 and placement of the distal end of the embryo transfer catheter 28 within the embryo dish within the incubator. The added length in these situations would create handling and manipulation challenges for the embryologist. The handle 120 can reduce the amount of working length occupied by the handle 120 and controller 118 mechanism while still providing a one-handed operation to the advancement of the inner catheter 10 during use. The handle 120 contains gear wheel controller 118 mechanism for engaging and translating the inner catheter 10 during use. The handle 120 can have a posterior section that can be curved to fit the palm and fingers of the physician without requiring the inner catheter 10 to be placed through the handle 120 portion for engagement with the controller 118 mechanism. The handle 120 can have a pistol grip with gear wheels actuated by the thumb. The handle 120 can be incorporated into an everting catheter system 106 for use with transvaginal ultrasound.

Figure 14A:
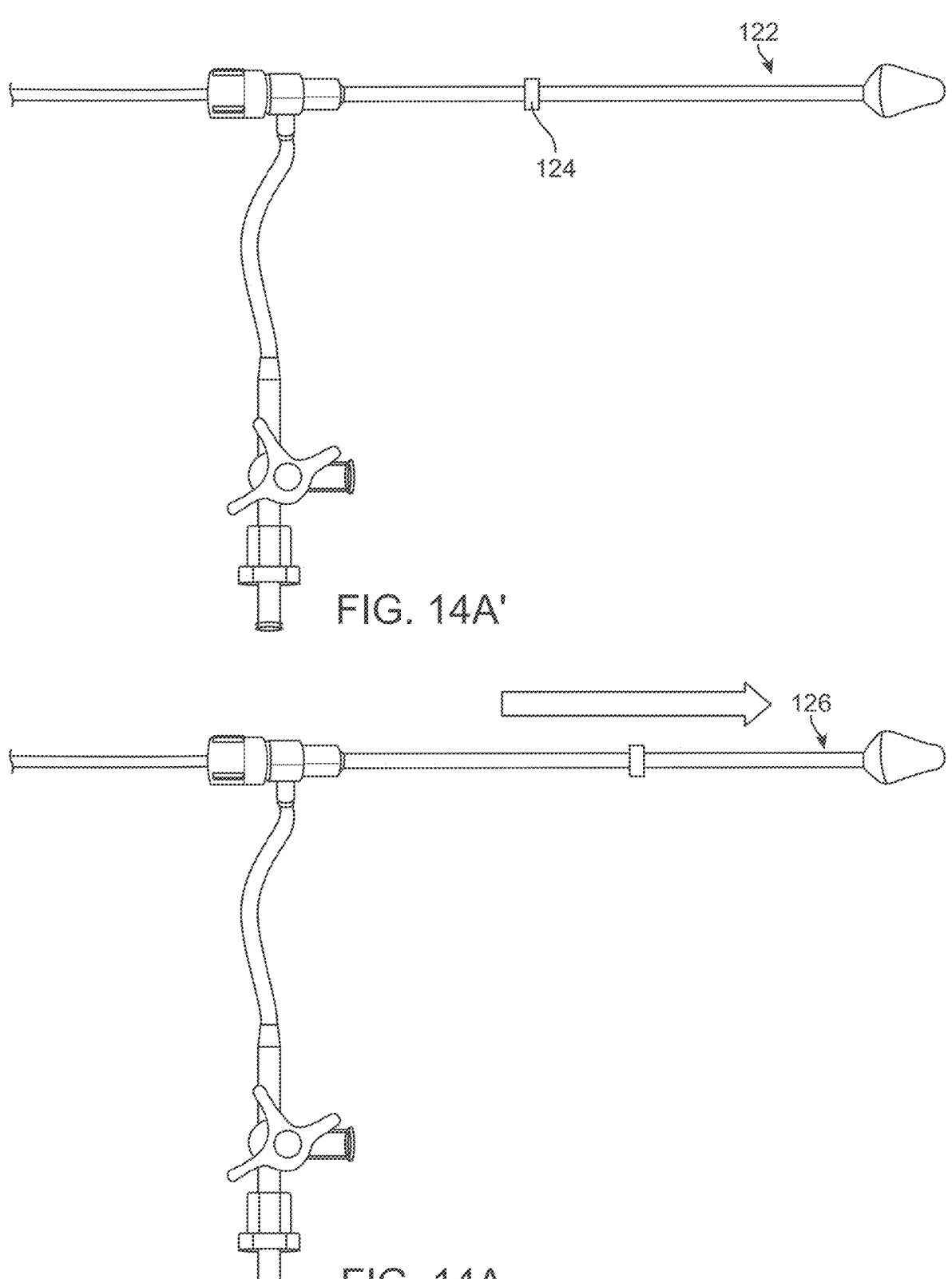
FIGS. 14A and 14A' illustrate side views of variations of the everting catheter balloon system that can have a translatable and adjustable distal end tip that can alter the working length of the everting balloon.

FIGS. 14A and 14A' illustrate that the everting balloon system 8 can have a translatable and adjustable distal end tip 122 that can alter the working length of the everting balloon 122. The translatable and adjustable distal end tip 122 can have a connector 124 on its proximal end and an acorn tip 110 on its distal end that can be advanced or retracted on the distal end of the delivery catheter 112. Advancement of the translatable and adjustable distal end tip 126 can reduce the overall length of the everting balloon 122 within the bodily cavity without impacting the markings on the proximal end of the embryo transfer catheter 28.

Figure 14B:
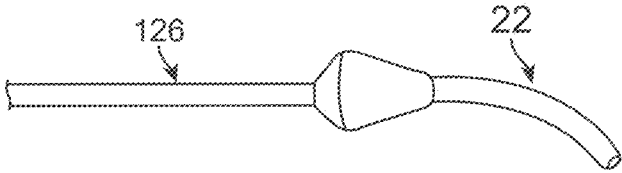
FIGS. 14B and 14B' illustrate a variations of the translatable and adjustable distal end tip at an extended position with resultant working length of the everting balloon.
Figure 14B:
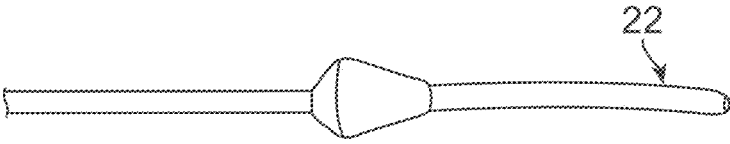

FIGS. 14B and 14B' illustrate that the translatable and adjustable distal end tip can be at an extended position with the resultant working length of the everting balloon 122. As an example, the everting balloon system 8 can have a 5 cm long everting balloon 22 has the translatable and adjustable distal end tip advanced 3 cm on the delivery catheter 32. The resultant new working length of the everting balloon 22 in the body cavity can be 2 cm. The connector 124 on the proximal end of the translatable and adjustable distal end tip can be rotated to engage edges of D-shape outer tubing 54 of the delivery catheter 32. Once rotated in the locked position, the translatable and adjustable distal end tip can no longer move or slide on the delivery catheter 32. Unlocking the connector 124 by rotation will return translational movement to the translatable and adjustable distal end tip. Other types of connectors 124 are possible including twist valve that resist movement by friction on the outer tube of the delivery catheter 32 and can be untwisted to allow movement. Another example of a connector 124 is a clip that has an engaged and disengaged position which is actuated by the user.

FIGS. 15A and 15A' illustrate a protective tube system 128 for the embryo transfer catheter 28 that facilitates handling and transport of the catheter. The protective tube can be shipped assembled with two tube components with male and female connections 130 attached to each other with the embryo transfer catheter 28 within the lumen of the protective tube.

FIGS. 15B, 15B', and 15B" illustrate a protective tube system 128 for the embryo transfer catheter 28 in the detached configuration for the loading of embryos. The female connection can be at the protective tube female end 132. The female connection of the tube component can be separated from the male connection 134 at a point near the distal end of the embryo transfer catheter 28, leaving a distal portion of the embryo transfer catheter 28 exposed for working under microscopic vision and the loading of embryo(s) and/or reproductive materials. FIG. 15B" shows the handling of the embryo transfer catheter 28 and the exposure of the embryo transfer catheter distal end 36 when loading embryos with an embryology syringe 66.

Figure 15C:
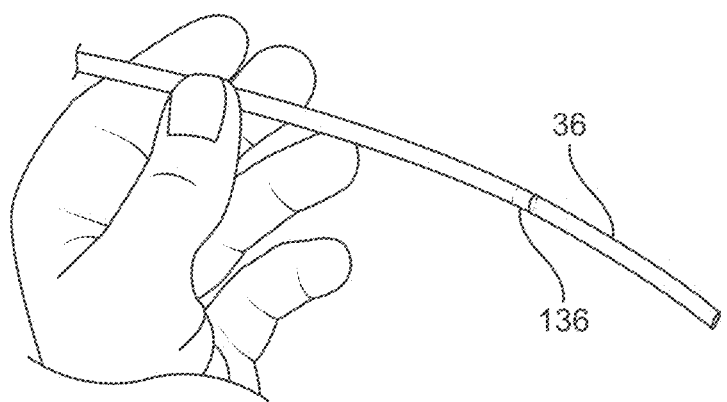
FIG. 15C illustrates a protective tube system for the embryo transfer catheter in the re-attached mode for the transport of the embryo transfer catheter.

FIG. 15C illustrates a protective tube system 128 for the embryo transfer catheter 28 in the re-attached configuration to cover the embryo transfer catheter distal end 36 with the protective tube, for example, for the transport of the embryo transfer catheter 28. Once loaded with embryo(s) and reproductive materials, the female connection can be reattached to the male connection for transport to the patient and the delivery catheter 32 system. The connection point 136 (between the male and female connections 130) in the protective tube can be opened to gain access to the distal end of the embryo transfer catheter 28 for manipulation under a microscope or within an embryology incubator. The connection point 136 can be re-attached for eventual transport to the patient and the completion of the embryo transfer procedure.

Figure 16:
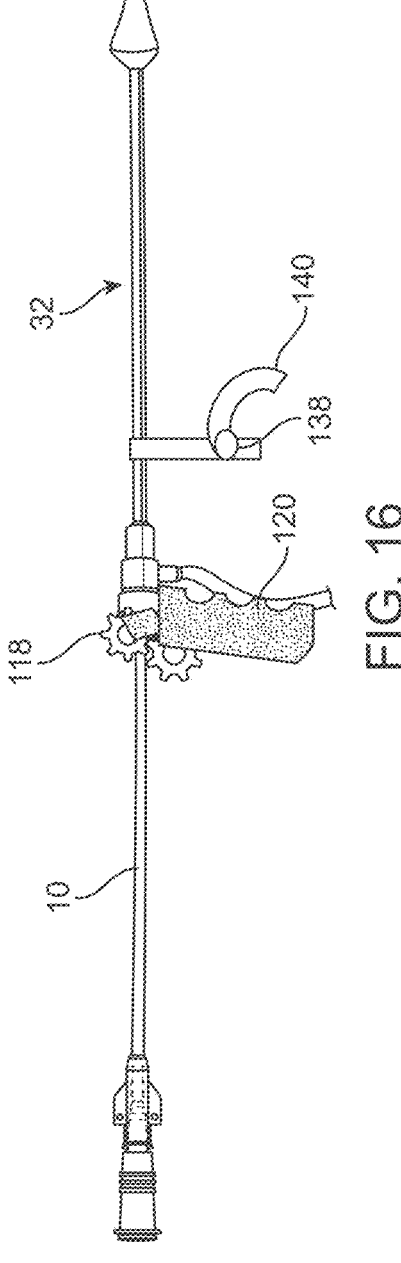
FIG. 16 illustrates an everting catheter system that has a coupling element to attach to the TUS probe.

FIG. 16 illustrates an everting catheter system 106 that has a coupling element to attach to the TUS probe. The coupling element is attached to the delivery catheter 32 portion of the everting catheter system 106. The coupling element can have a probe attachment clip 140 that can attachably engage or fit onto the shaft of a transvaginal ultrasound (TUS) probe. The clip can have an arm that can encircle and attach to the TUS probe and the arm is rotated about a pin 138 to clamp onto the TUS probe. The pin 138 can be attached to a rotating clip on the TUS probe. The attachment of the everting catheter system 106 to the TUS probe can allow the physician to hold onto the TUS probe while maintaining the position of the everting catheter system 106 in situ, thereby leaving a hand free to pass a transfer catheter, or actuate controls on the ultrasound console, or steady the patient. Importantly, the coupling element while attached to the TUS probe allows the physician to control the visualization of the ultrasound imaging while actuating the everting catheter 218, passing a transfer catheter, making the deposition of reproductive matter into the uterine cavity, and removing the entire system from the patient's uterine cavity; all while under direct ultrasound visualization control of the physician.

Figure 17A:
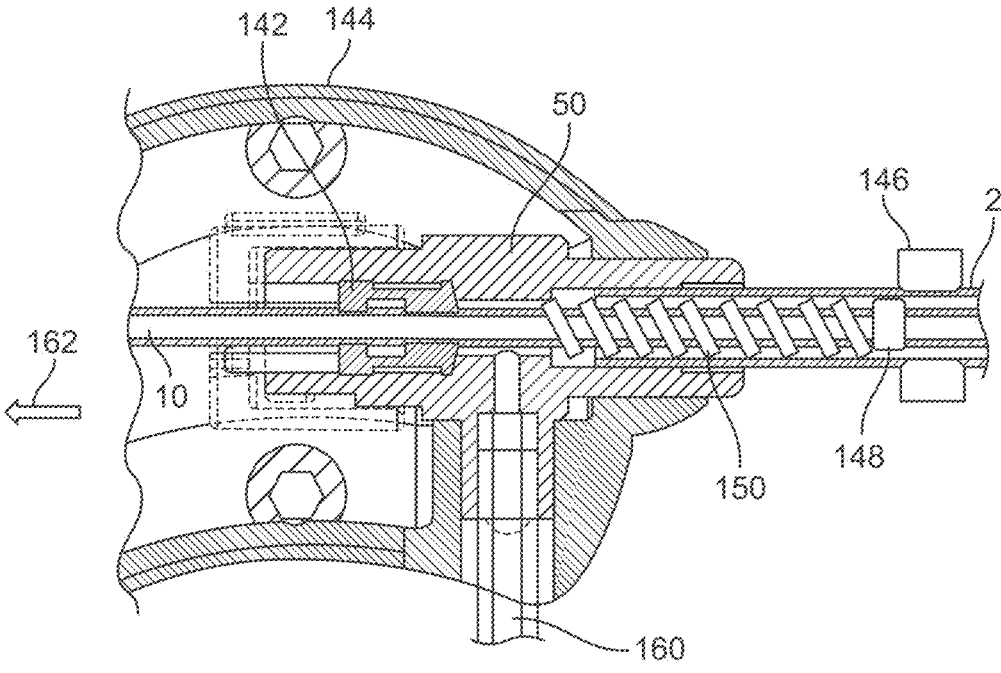
FIG. 17A illustrates an everting catheter system with a spring loaded inner catheter for automatically translating the inner catheter.

FIG. 17A illustrates an everting catheter system 106 with a spring 150 loaded inner catheter 10 for automatically translating the inner catheter 10. Fluid 70 can be delivered through the fill port 94 and/or inflation lumen 160, for example, to pressurize the balloon membrane 6. A spring 150 can be contained within the outer catheter 2 and surrounds the inner catheter 10. The inner catheter 10 is retracted with the everting balloon membrane 6 inverted within the outer catheter 2. A spring stop 148 can be on or otherwise attached to the inner catheter 10 and extend radially outward from the inner catheter 10. The spring 150 can be compressed in the retracted state by the spring stop 148 against the Y-fitting 50 that contains the Touhy-Borst mechanism with the Touhy-Borst gasket 142 to maintain internal pressurization of the everting catheter system 106. The Touhy-Borst gasket 142 can seal around the inner catheter 10. The spring compression can occur when the inner catheter 10 is placed in the retracted state with the everting balloon 22 inverted. The spring 150 can be locked in place by the spring button (also referred to as the release button 146). The spring button can provide a mechanical restriction to hold the spring stop 148 in place once retracted. (The release button 146 can be on the outer catheter 2. The release button 146 can be for releasing the spring 150 and allowing the inner catheter 10 to advance within the outer catheter 2 and advancing the balloon membrane 6 in conjunction with balloon pressure.) When the outer portions 144 of the Spring stop 148 are compressed by the physician, the spring button internal diameter opens and allows the compressed spring 150 to open and push against the spring stop 148. This allows the inner catheter 10 to advance and release the everting balloon membrane 6. The speed or rate of movement of the inner catheter 10 is governed by the resistance caused by friction within the gasket in the Y-fitting 50. The rate of movement of the everting balloon 22 should be within a speed that allows for easy observation by the physician with ultrasound imaging. Too rapid eversion may be clinically unacceptable or may cause discomfort to the patient. Eversion that is too slow may prolong the procedure unnecessarily. In numerical terms, the rate of clinically acceptable inner catheter 10 advancement ranges from 5 to 20 seconds for complete eversion of a 5 cm length of balloon. Alternatively or in combination with the friction within the gasket, the rate of movement forward of the inner catheter 10 can be restricted or regulated by mechanical dampeners (not shown), dash-pots which slow movement, ratchets 190 that control the rate of movement in step-wise movements, or wheels with gearing that slow the rate of movement which can limit the speed in which the inner catheter 10 advances within the outer catheter 2. In the configurations described above, once the everting catheter system 106 is pressurized, the advancement of the inner catheter 10 and everting balloon membrane 6 can occur automatically in a slow fashion, or since the proximal end of the inner catheter 10 is accessible, the rate of movement can be observed and over-ridden directly by the physician by manipulating the proximal portion of the inner catheter 162 in conjunction with the automatic advancement mechanism. In the configurations above, energy is stored by a spring 150 that is compressed. The force required to move or advance the inner catheter 10 while pressurized, and within a clinically acceptable rate of movement, can be determined by measuring the force and selecting a spring 150 and spring constant that while under compression provides the necessary force for movement. Alternatively the spring 150 can be wound or rotated to create stored energy.

Figure 17B:
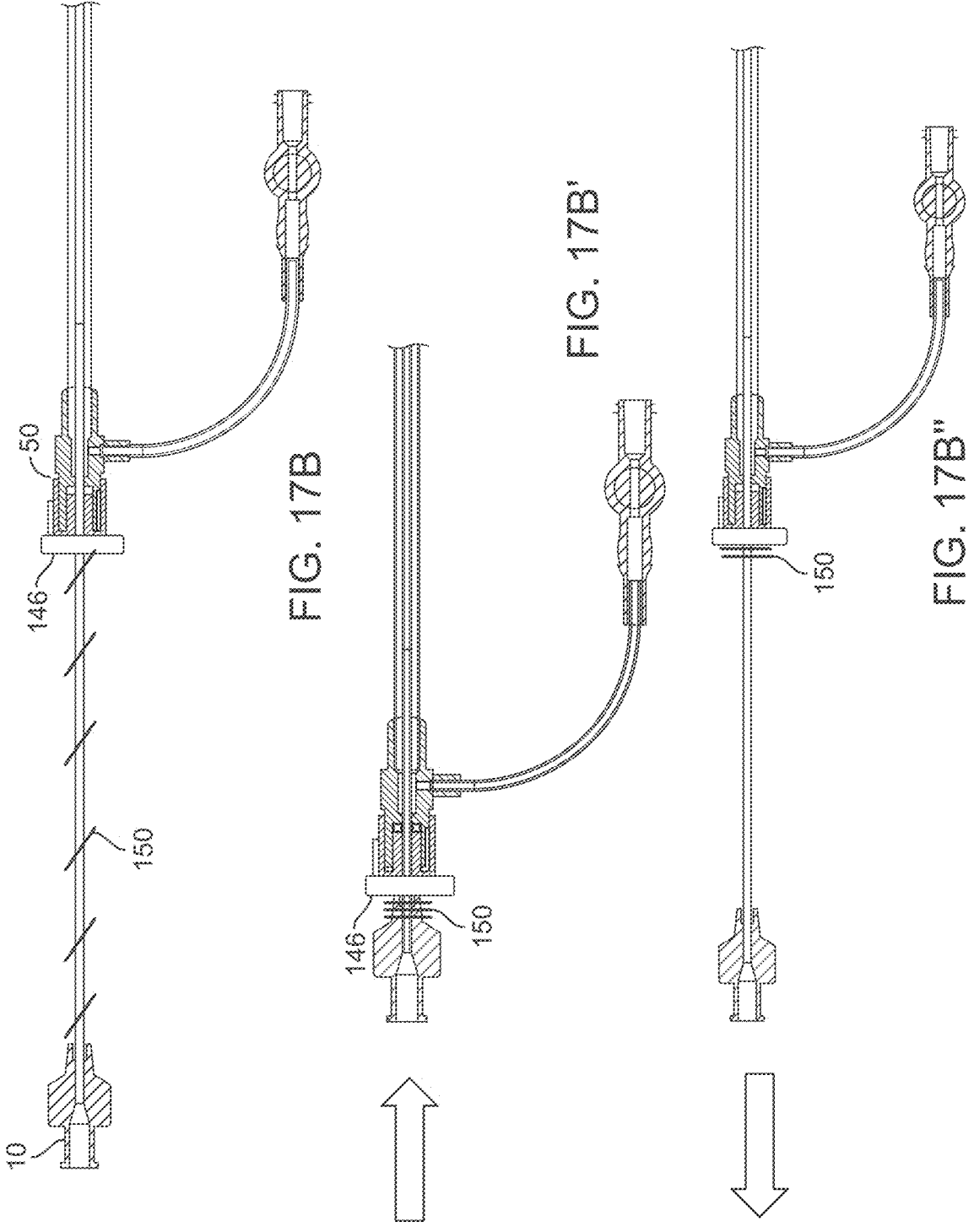
FIGS. 17B, 17B', and 17B" illustrate a variation of an everting catheter system with a spring loaded inner catheter for automatically translating the inner catheter.

FIGS. 17B, 17B', and 17B" illustrate that the everting catheter system 106 can have a spring loaded inner catheter 10 for automatically advancing the inner catheter 162 for the eversion process for the deposition of reproductive matter in the uterine cavity. The spring 150 can be located on the proximal portion of the inner catheter 184. When the inner catheter 10 is fully retracted, energy can be stored in a spring 150 in a fully extended or retracted position. The spring 150 can urge the advancement of the inner catheter 10 when the spring 150 is released. The rate or speed of movement of the inner catheter 10 can be governed or regulated by the friction in the gasket in the Touhy-Borst. In addition, the rate of movement forward of the inner catheter 10 can be restricted or regulated by mechanical dampeners, dash-pots which slow movement, ratchets 190 that control the rate of movement in step-wise movements, or wheels with gearing that slow the rate of movement which can limit the speed in which the inner catheter 10 advances within the outer catheter 2.

FIG. 17B illustrates that the system can have a Toughy-Borst Y-fitting 142 with an internal gasket. The release button 146 can be depressed to Release button 146 to allow the inner catheter 10 to advance.

FIG. 17B' illustrates that the spring 150 can be in its natural, unstressed state when advancement of the inner catheter 10 is completed. At the completion of the eversion process, the release button 146 can disengage to allow the inner catheter 10 to be retracted.

FIG. 17B" illustrates that once disengaged, the spring 150 remains and allows for the inner catheter 10 to be retracted.

Figure 17C:
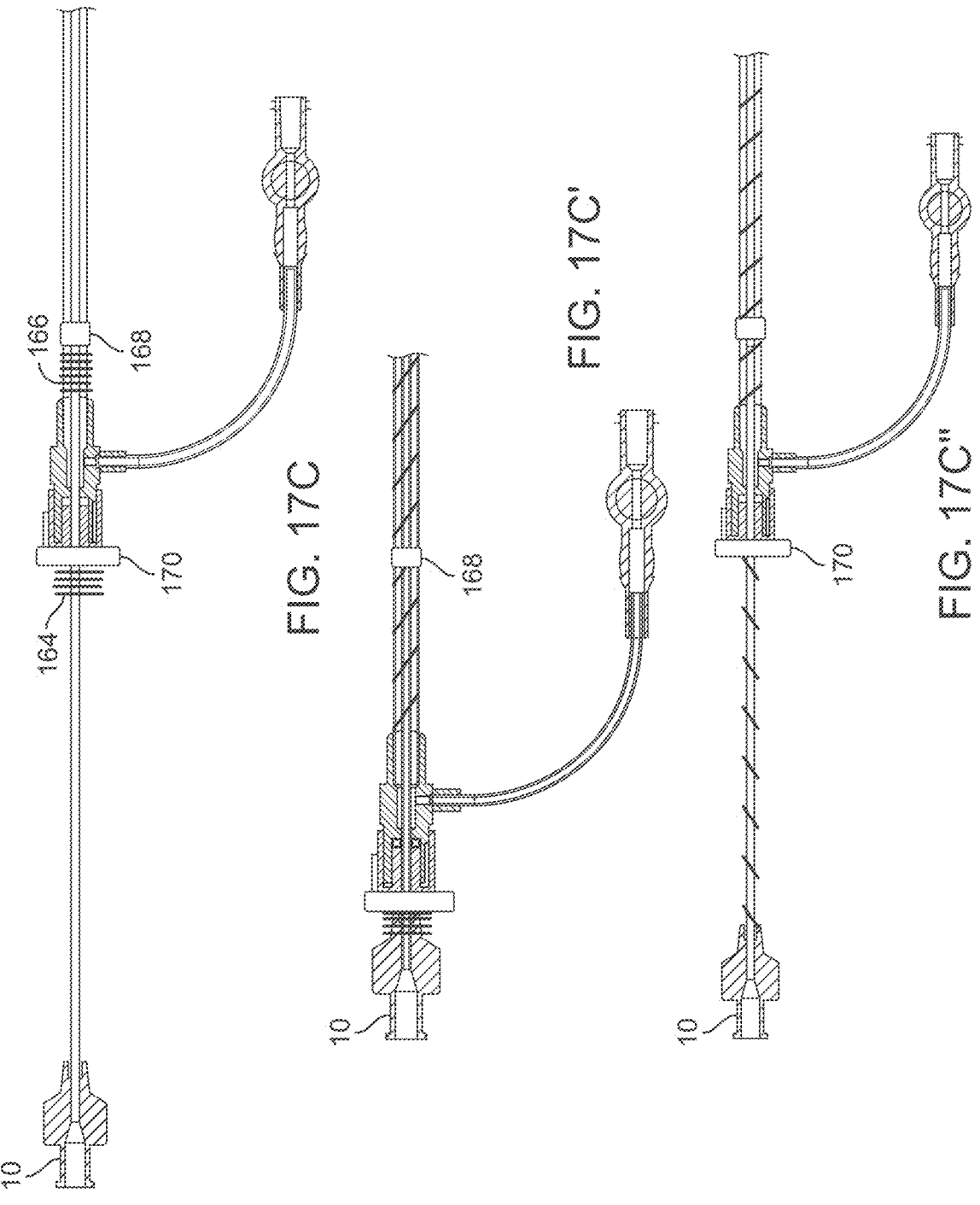
FIGS. 17C, 17C', and 17C" illustrate a variation of an everting catheter system with a spring loaded inner catheter for automatically translating and retracting the inner catheter.

FIGS. 17C, 17C', and 17C" illustrate that the everting catheter system 106 can have a spring 150 loaded inner catheter 10 for automatically translating and retracting the inner catheter 10. The first and seconds can be located on opposing positions of the inner catheter 10 and by selectively storing energy, and releasing energy of one spring 150, and then the contralateral spring 150, can create both the advancement and retraction of the inner catheter 10. Both springs 150 can be compressed at the start of the procedure but restrained in the held (e.g., compressed) position. The everting balloon system 8 can be pressurized. The first spring 166 can be released by actuating the first release button 168 to allow the advancement of the inner catheter 10. Once the eversion process has been completed, the first spring 166 can be no longer engaged with the spring stop 148. At the completion of the eversion process, the inner catheter 10 can then be positioned for the action to be created by the second spring 164. After the deposition of reproductive matter into the uterine cavity, the second spring 164 can be released by actuating the second release button 170 to retract the inner catheter 10. Concurrent with the advancement and retraction of the everting catheter system 106, the physician can maintain control of the TUS probe while only requiring the button release of the first and second spring 164 for the eversion and inversion process. The system can have a single release button 146 that can toggle between the two functions (releasing the first spring 166 and the second spring 164) mentioned above.

FIG. 17C illustrates that the inner catheter 10 can be retracted at the beginning of procedure with the everting balloon 22 pressurized. The first spring 166 can be in position and in a compressed state. The second spring 164 can be in position and in a compressed state.

FIG. 17C' illustrates that inner catheter 10 can be advanced and the balloon can be allowed to evert. The first release button 168 can be actuated. The advance inner catheter 10 can be advanced and the pressurized balloon can be everted.

FIG. 17C" illustrates that the second release button 170 can be actuated. The inner catheter 10 can retract and the pressurized balloon can be inverted. After deposition of reproductive matter in the uterine cavity, actuation of the second release button 170 can retract the inner catheter 10 and the balloon can be allowed to invert.

Figure 17D:
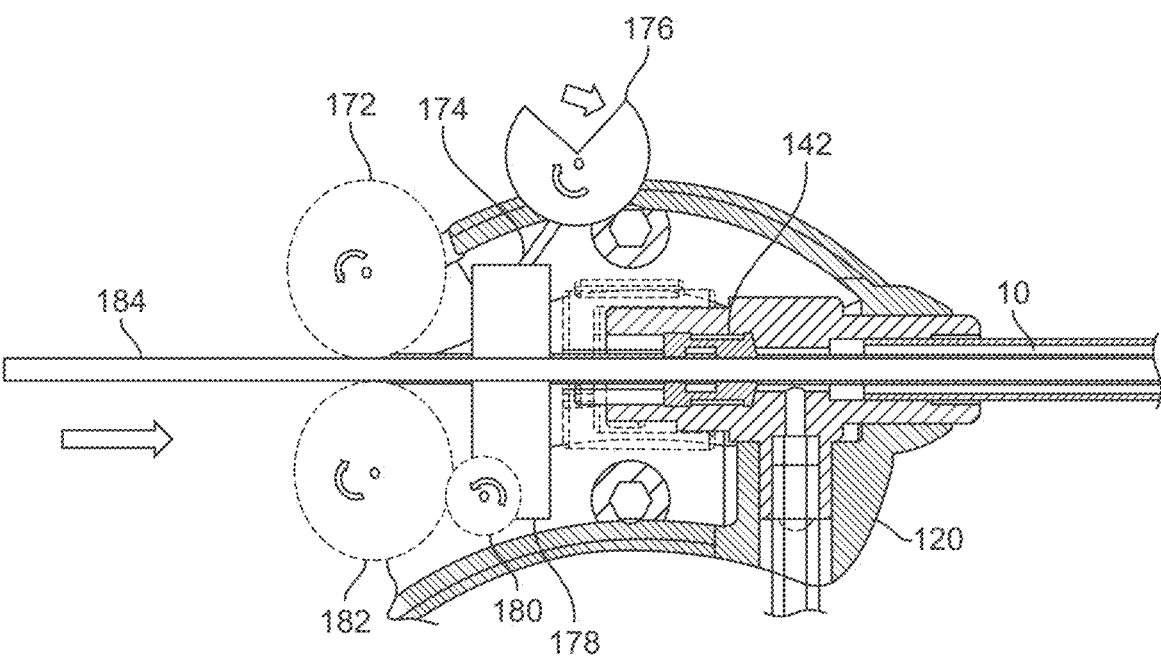
FIG. 17D illustrates an everting catheter system with a motor coupled to the inner catheter for automatically translating and retracting the inner catheter.

FIG. 17D illustrates an everting catheter system 106 with a motorized mechanism for the advancement and retraction of the inner catheter 10 when the everting balloon membrane 6 is pressurized. The system can have a handle 120 which is holding within itself a Touhy-Borst gasket 142, a motor and battery 178 can be housed with a rotating motor gear wheel 180. The motor and battery 178 can be activated by a toggle switch 176 connected by a toggle wire 174 which can direct the starting, ending, and direction of the gear wheel. Coupled to the gear wheel can be a traction wheel 182.

The system can have a Rotation Wheel 172 to guide advancement and retraction of the inner catheter 10. The Traction Wheel 182 can be connected to Motor Gear Wheel 180 for advancement and retraction of the inner catheter 10. The motor gear wheel 180 can be connected to the motor and the battery. The motor and the battery can be connected to a toggle wire 174. The toggle wire 174 can be connected from a toggle switch 176 to the motor and battery to turn the motor on and off and reverse its direction. The toggle switch 176 can turn the motor on and off and reverse its direction for the advancement and retraction of inner catheter 10.

The everting balloon membrane 6 can be connected to the inner catheter 10 distal end.

The traction wheel 182 can engage the inner catheter 10 for automatically translating and retracting the inner catheter 10. A guide wheel can secure the contact of the inner catheter 10 to the traction wheel 182. Once the everting balloon membrane 6 is pressurized, a forward push on the toggle switch 176 can activate the motor and battery 178 to advance the gear wheel to rotate the traction wheel 182. Once the deposition of reproductive matter to the uterine cavity is completed, the toggle switch 176 can be pushed in the opposite or backward direction to initiate retraction of the inner catheter 10.

FIGS. 18A through 18E illustrate speculums and their mechanisms for opening the vagina for the insertion of devices for transvaginal procedures. Vaginal speculums are designed to expose the cervix 202 so that the physician can directly visualize the exocervix.

Figures 18A, 18B, 18C, 18D, 18E:
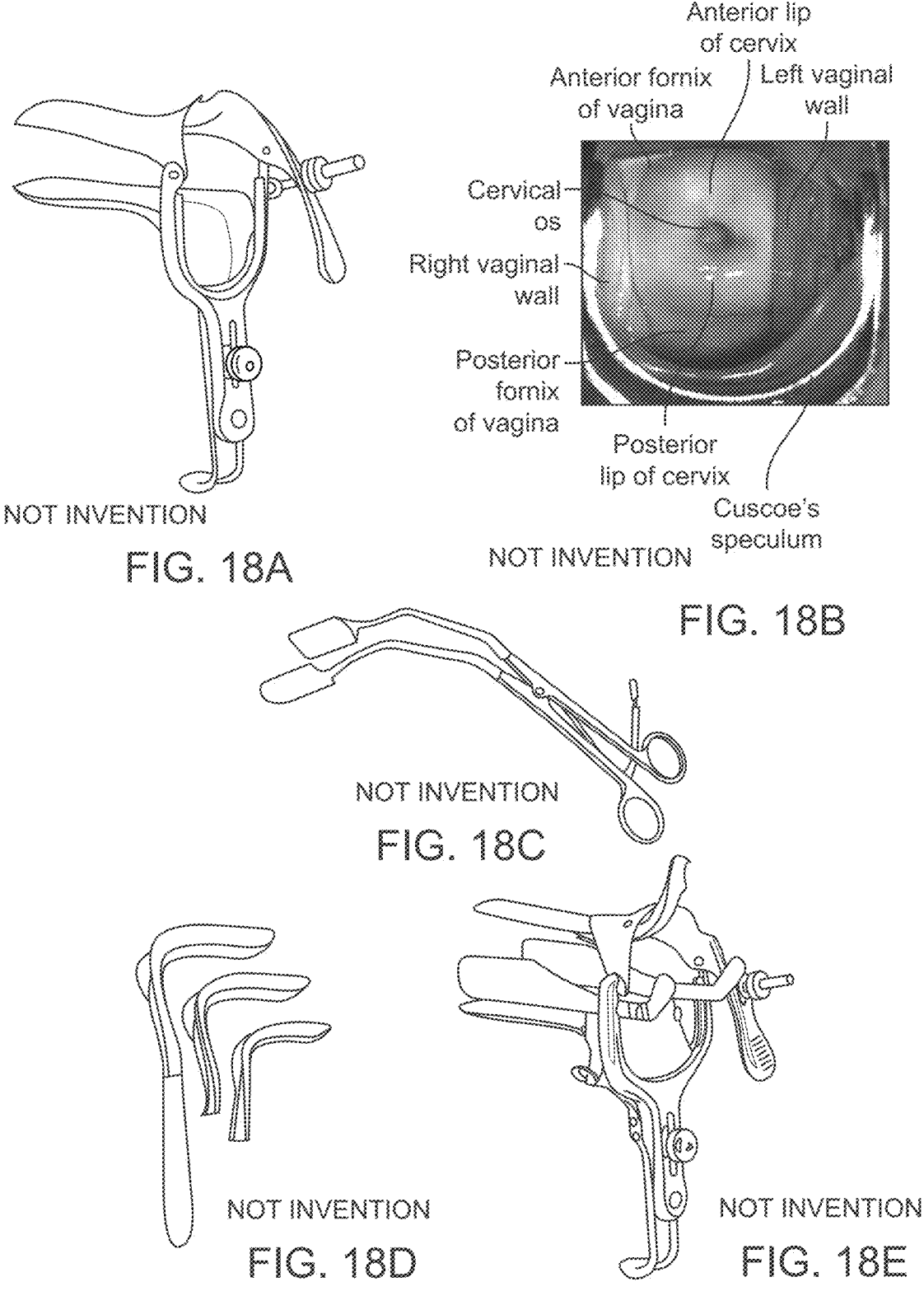
FIGS. 18A through 18E illustrate variations of speculums that are not the invention.

FIG. 18A illustrates a standard bi-valved, two blade (duckbill) vaginal speculum with anterior and posterior wall opening mechanism.

FIG. 18B illustrates a cervix 202 with a standard vaginal speculum with an anterior and posterior wall opening mechanism. Also shown is the circumferential housing of a bi-valved vaginal speculum.

FIG. 18C illustrates a lateral wall opening speculum.

FIG. 18D illustrates a Sims speculum having a single arm for opening the posterior or anterior wall.

FIG. 18E illustrates a 4-way (4 blades) opening speculum with anterior, posterior, and lateral wall opening blades.

The most common vaginal speculums have arms or blades 186 for displacing the anterior and posterior walls of the vagina. The standard vaginal speculum is bi-valved with two blades 186 and has a duckbill appearance. These vaginal speculums come in multiple sizes and lengths with ratcheting mechanisms to maintain the opening of the vagina 200. Some vaginal speculums have a continuous circumferential housing to contain the mechanism for opening or separating the blades 186 and applying pressure on the anterior and posterior walls of the vagina. Some speculums have a side-opening housing that allows the speculum to be slipped out of the vagina while allowing the devices to remain in place. In practice, IVF specialists need to remove the vaginal speculum to effectively operate the TUS probe which becomes increasingly difficult with embryo transfer catheter 28 systems that require two hands for effective operation. Alternatively Sims speculums, or single arm or single blade 186 speculums, have a separate posterior arm component that has a separate anterior arm component for opening the vagina. The Sims speculum used in the posterior aspect of the vagina can be inserted sideways to minimize the insertion profile. Secondarily, the arm can be rotated so that the flat portion of the Sims speculum arm is horizontal to the vaginal opening to thereby open the bottom portion of the vagina. The flat arm provides pressure on posterior vaginal opening and conversely, an anterior Sims speculum or single-arm speculum will provide pressure on the anterior opening of the vagina 200. When using Sims speculum arms on both the anterior and posterior walls, this requires two physicians or operators and the arms can be slipped out separately to allow for devices to remain in place in the vagina. Another type of vaginal speculums are designed to open only the lateral walls of the vagina as opposed to the anterior and posterior walls of the vagina. Yet another type of vaginal speculum contains four arms that opens the anterior, posterior, and both lateral walls of the vagina. In addition, some speculums are configured with 3 blades. For all of these vaginal speculums, they are designed to open the vagina to provide visual and manual access to the cervix 202 for transvaginal procedures.

For clinical practice, the IVF specialist will wash the exocervix prior to the insertion of the embryo transfer catheter 28 system. Besides clearly visualizing the cervical opening, the IVF specialist does not want vaginal fluids or bacteria on the cervix 202 or within the vagina to come into contact with the embryo transfer catheter 28 system during the insertion of catheters within the endocervix and then the uterine cavity. An additional purpose of the vaginal speculum is to keep tissues from the vaginal walls away from the cervix 202 so that the embryo transfer catheter 28 system does not come into contact with the labia or inner vaginal walls during the insertion process. The size and physical presence of the vaginal speculum does not facilitate the insertion and operation of a TUS probe in combination with standard embryo transfer catheter 28 systems that require multiple hands to effectively operate. In particular, TUS probes are designed to be placed at back wall of the vagina at the anterior fornix next alongside the cervix 202. And further, it has been reported in medical literature that the physical manipulation of the vaginal speculum can incite uterine contractions which are not desirable for IVF procedures which require the implantation of embryos. In addition, female patients have reported discomfort with the manipulation of vaginal speculums in the process of retracting the vaginal walls to expose the cervix 202. Using smaller, lower profile vaginal speculums or pediatric speculums would be more comfortable for the patient and reduced physical size and reduced vaginal manipulations will thereby lower the incidence of subsequent uterine contractions. Unfortunately the operation of existing embryo transfer catheter 28 systems require two hands and necessitate greater vaginal openings. As well as room to avoid inadvertent contact with the vaginal walls during the catheter insertion process. Use of Sims single-arm speculums and flat arms on outermost opening of the vagina 200 provoke pressure on the posterior or anterior openings of the vagina. To summarize, a vaginal speculums that are designed to function with a lower profile and can be used in conjunction with an embryo transfer catheter 28 system would be a benefit.

FIGS. 19A to 19D illustrate a speculum system that can be suited for working with the everting catheter system 106. The speculum can be designed for positioning at the posterior aspect of the vaginal opening with angled walls that fan open. The configuration of the speculum can minimize radial pressure on the vaginal walls and provide enough opening space to visualize the cervix 202 and/or insert a TUS probe. The everting catheter system 106 can be operated with one hand. The everting catheter system 106 can have the components that contact the endocervix and uterine cavity within the delivery catheter 32, for example to avoid contamination by touching the vaginal walls and to minimize the need for making a large vaginal opening (e.g., as with a standard speculum).

Figure 19A:
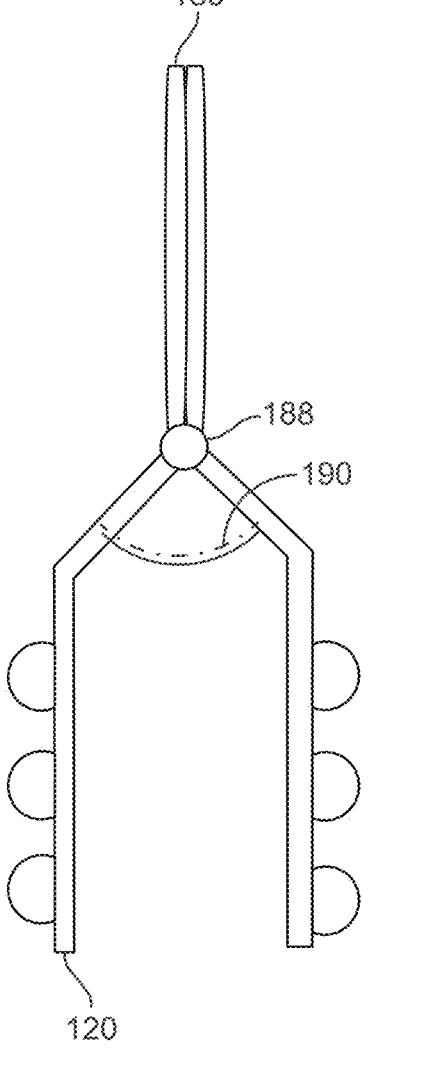
FIGS. 19A, 19A' and 19B illustrate variations of the speculum.
Figure 19A:
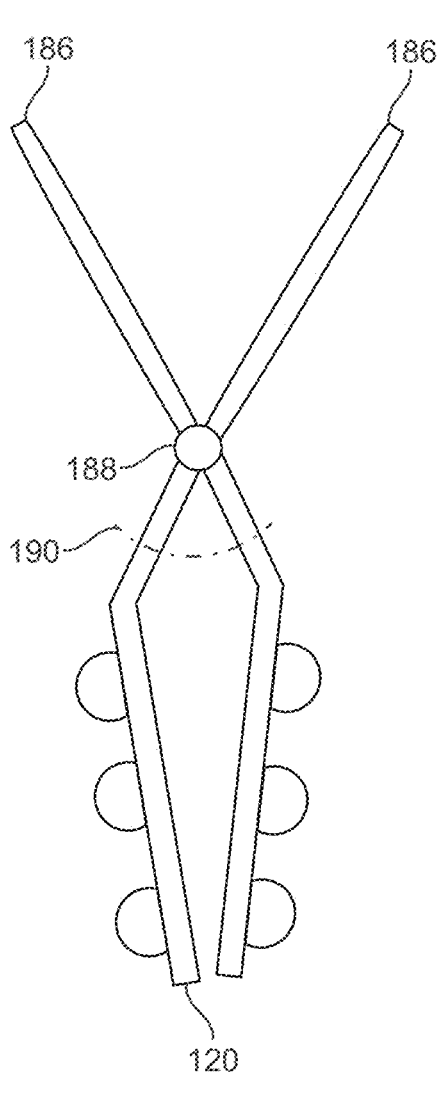

FIGS. 19A and 19A' illustrate the operation of the speculum in an axial view looking from the proximal end of the speculum. As shown in FIG. 19A, the two blades of the speculum can be nested in each other during the insertion process. Manipulation (e.g., squeezing together or rotation toward the other side) of the handle 120 can open the blades at the lowest, posterior point to the angle desired by the physician. The handle 120 can have a ratchet 190 mechanism to lock the blades at a desired angle in the open position. The contralateral blades and handles can rotate about an axis point 188 (also referred to as the central axis 216), such as a pin 138 or pivot.

Figure 19B:
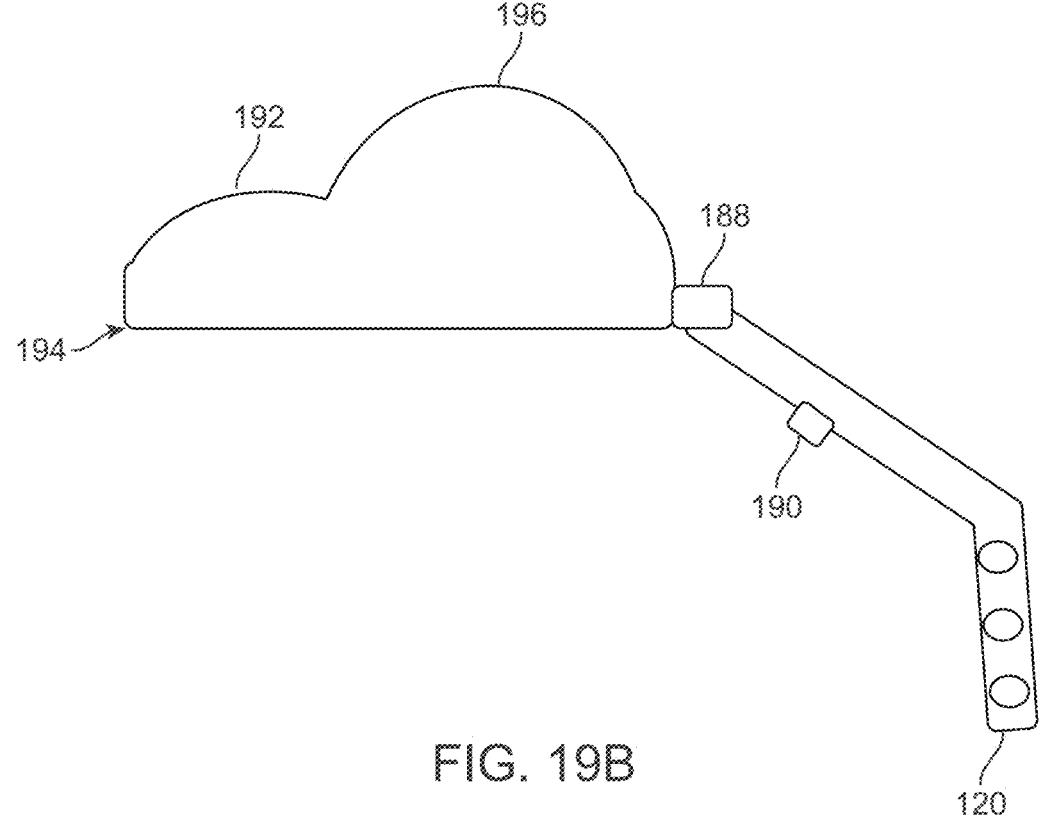
FIGS. 19C and 19D illustrate variations of the speculum during use with the TUS probe.

FIG. 19B illustrates the speculum in a side view with the handles squeezed together. The speculum can have a speculum distal end 194. The blades 186 can each have a larger proximal projection 196 and a smaller distal projection 192. The projections can be curved. The larger projections of the blades 186 can be directed towards the exterior portion of the vagina. The larger proximal projections 196 can open the exterior portion of the vagina at the posterior angle created by the central axis 216 point of the speculum. The smaller distal projection 192 can be placed near the cervix 202 and can allow for greater room for placement of the TUS probe. The axis point 188 can be a central axis 216 and can form a posterior angle between the blades 186 and the portion of the speculum proximal to the axis point 188.

Figure 19C:
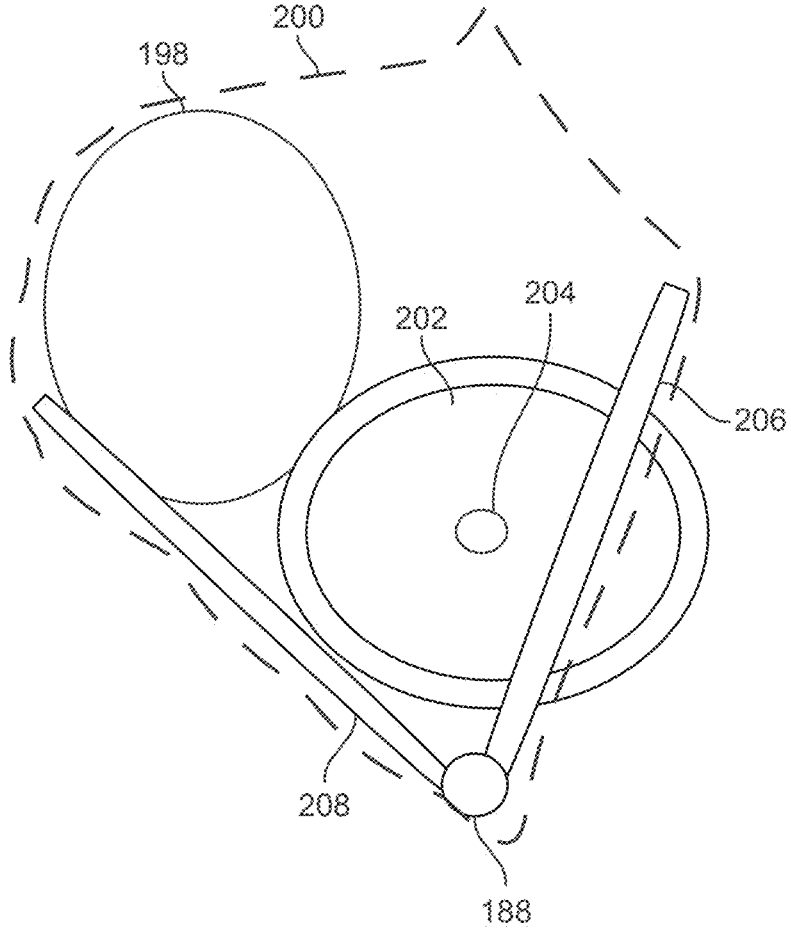

FIG. 19C illustrates the speculum in a diagrammatic format depicting the opening of the vagina 200 with a placement of a TUS probe in close proximity to the cervix 202 and the exocervial os 204 (the opening of the cervix 202). The left and right blades 186 can be opened to hold open the vagina and provide access to the cervix 202 and exocervial os 204 for visual inspection and/or placement of the TUS probe. The blades 186 can be angled, for example, toward the patient's right side to fit the TUS probe on the right side of the cervix 202. (During typical use, the left blade 208 will be on the patient's right side and the right blade 206 will be on the patient's left side.)

Figure 19D:
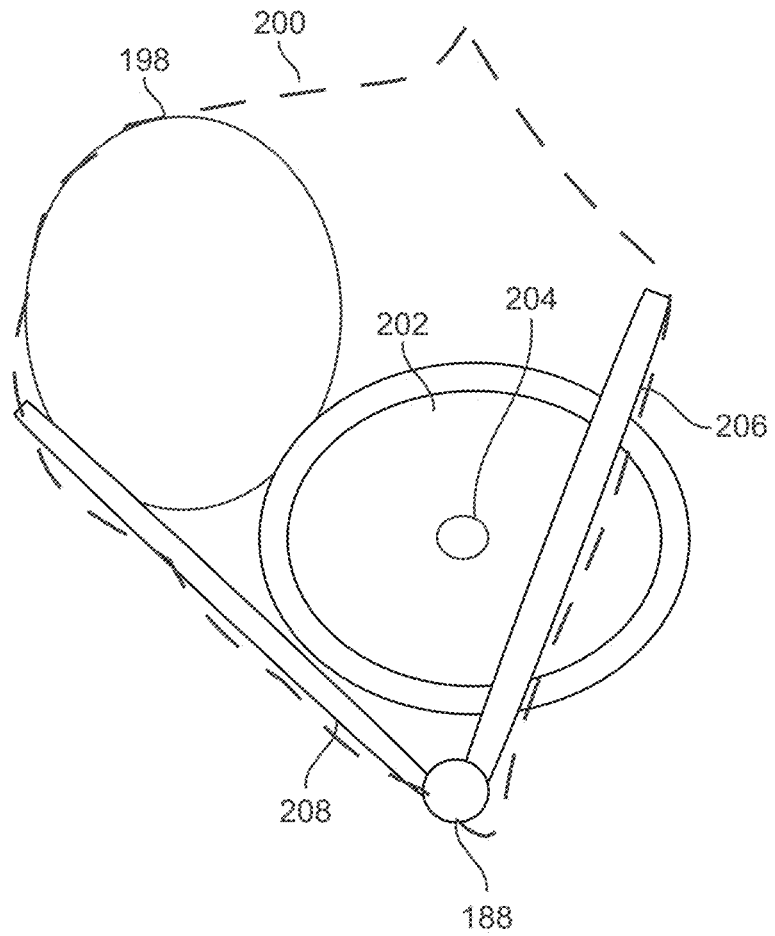

FIG. 19D illustrates the speculum in a diagrammatical view with the left blade 208 (fits on the patient's right hand side) that can have a smaller projection (i.e., height) than the right blade 206. The smaller left blade 208 can allow for greater room for the TUS probe when handled by the physician's left hand (e.g., leaving the right hand of the physician to operate the everting catheter system 106). The larger and smaller projections of the blades 186 can be reversed laterally or along the length, for example, if the physician prefers to use the right had for control of the TUS probe.

Figure 20:
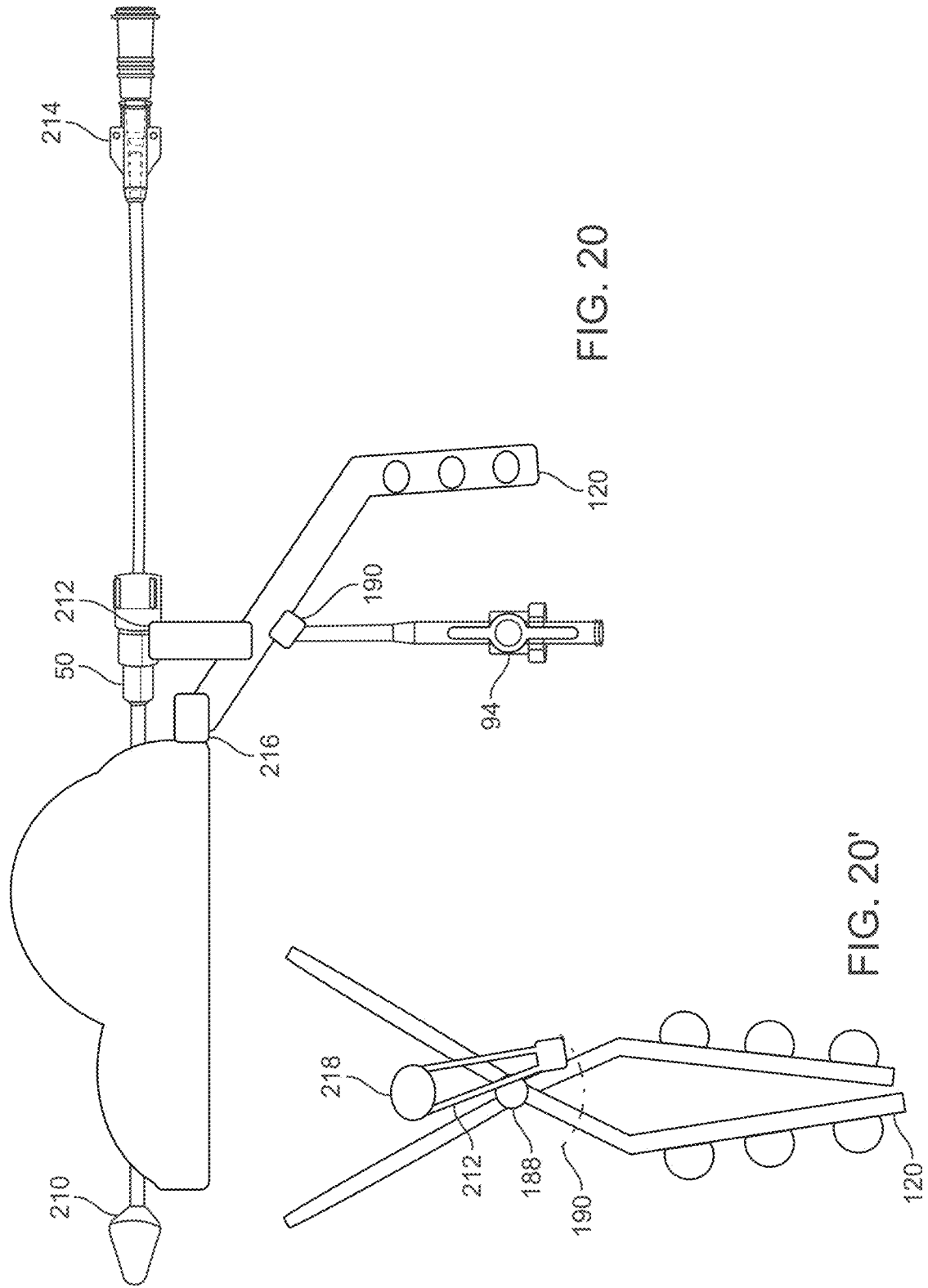
FIGS. 20 and 20' are side and axial views, respectively, of a variation of the speculum coupled to the everting catheter system.

FIGS. 20 and 20' illustrate the speculum with a speculum coupling mechanism 212 for an everting catheter system 106. Within the anterior surface of the central axis 216 of the speculum can be a coupling mechanism to place and/or attach to the everting catheter system 106. The coupling mechanism can allow the IVF specialist to place the everting catheter system 106 so that the position of the everting catheter 218 is maintained, allowing the physician to use his/her hands for advancing the embryo transfer catheter 28 and TUS probe.

Figure 21:
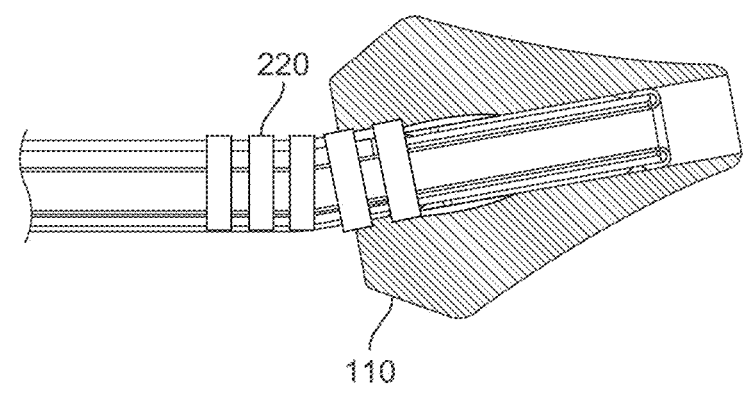
FIG. 21 illustrates an acorn tip at the distal end of an everting catheter that can be malleable.
Figure 21:
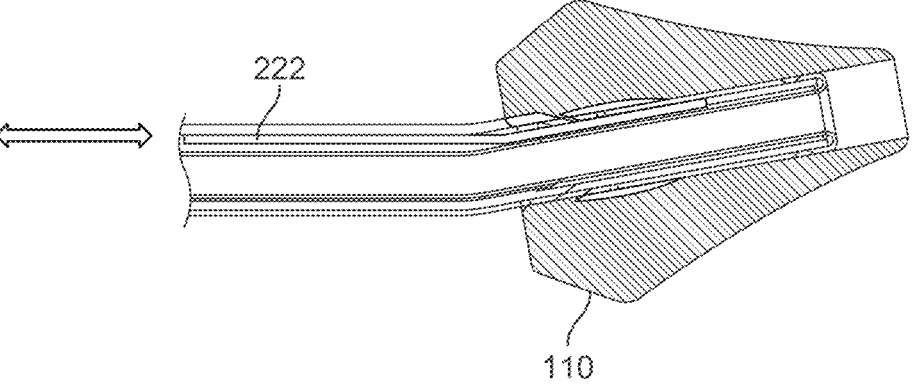

FIGS. 21 and 21' illustrate that an acorn tip 110 at the distal end of the everting catheter 218 can be malleable or articulatable, for example, to allow the distal end opening of the everting catheter system 106 to be directed towards the exocervix os (opening of the cervix 202). In the malleable tip design shown in FIG. 21, a deformable spring coil 220 can be bendable and hold the curve made on the distal end of the everting catheter 218 to direct the acorn tip 110 towards the opening of the cervix 202. A stainless steel mandrel can be supplied within the outer catheter 2 that can allow the physician to place a bend within the distal end of the catheter to direct the distal end opening towards the exocervical os 204.

FIG. 21' illustrates that the articulating distal end can have a pull wire 222 within the everting catheter 218 that can be configured to be pulled to change the angle of the tip and direct the distal end opening towards the exocervical ox of the patient. At the proximal end of the everting catheter 218, the physician can actuate, manipulate, or pull the pull wire 222 to bend the acorn tip 110 selectively. The everting catheter 218 can have multiple pull wires 222 located at different angles around the catheter to control the angle of the acorn tip 110 in multiple directions.

FIG. 22A illustrates that the distal end of an everting catheter 218 can have an acorn tip 110 that is detachable from the remainder of the everting catheter 218. The acorn tip 110 can have a soft, rounded tip.

FIG. 22A' illustrates the variation of the distal end of an everting catheter of FIG. 22A with the acorn tip 110 removed to reveal a penetrating tip 226 or member for insertion into the exocervical os 204. The penetrating tip 226 can be designed to penetrate slightly the exocervix os to allow entry of the everting balloon 22 into the endocervical canal. The outer surface of the catheter can have mechanical detents 224 that can be radially retractable and snap-fit or interference fit the radially inner surface of the acorn tip 110. The acorn tip 110 can be detachably connected to the mechanical detents 224.

FIG. 22B illustrates that the distal end of the everting catheter can have a retractable acorn tip 110. The outer surface of the catheter can have threads 228 that can helically engage matching threads 228 on the inner surface of the acorn tip 110.

FIG. 22B' illustrates that the acorn tip 110 can be rotated with respect to the everting catheter 218, causing the acorn tip 110 to helically proximally retract with respect to the everting catheter 218. For example, the acorn tip 110 can be pressed into and braced against the wall around the cervical entrance 38 at the end of the vagina while the everting catheter 218 is rotated. The same backward or rearward repositioning of the acorn tip 110 can occur by directly pushing the acorn tip 110 backward on the outer catheter 2. After the acorn tip 110 can be sufficiently retracted to reveal the penetrating tip 226 or member at the distal terminal end of the everting catheter 218. The penetrating tip 226 can insert into the exocervical os 204.

Figure 23:
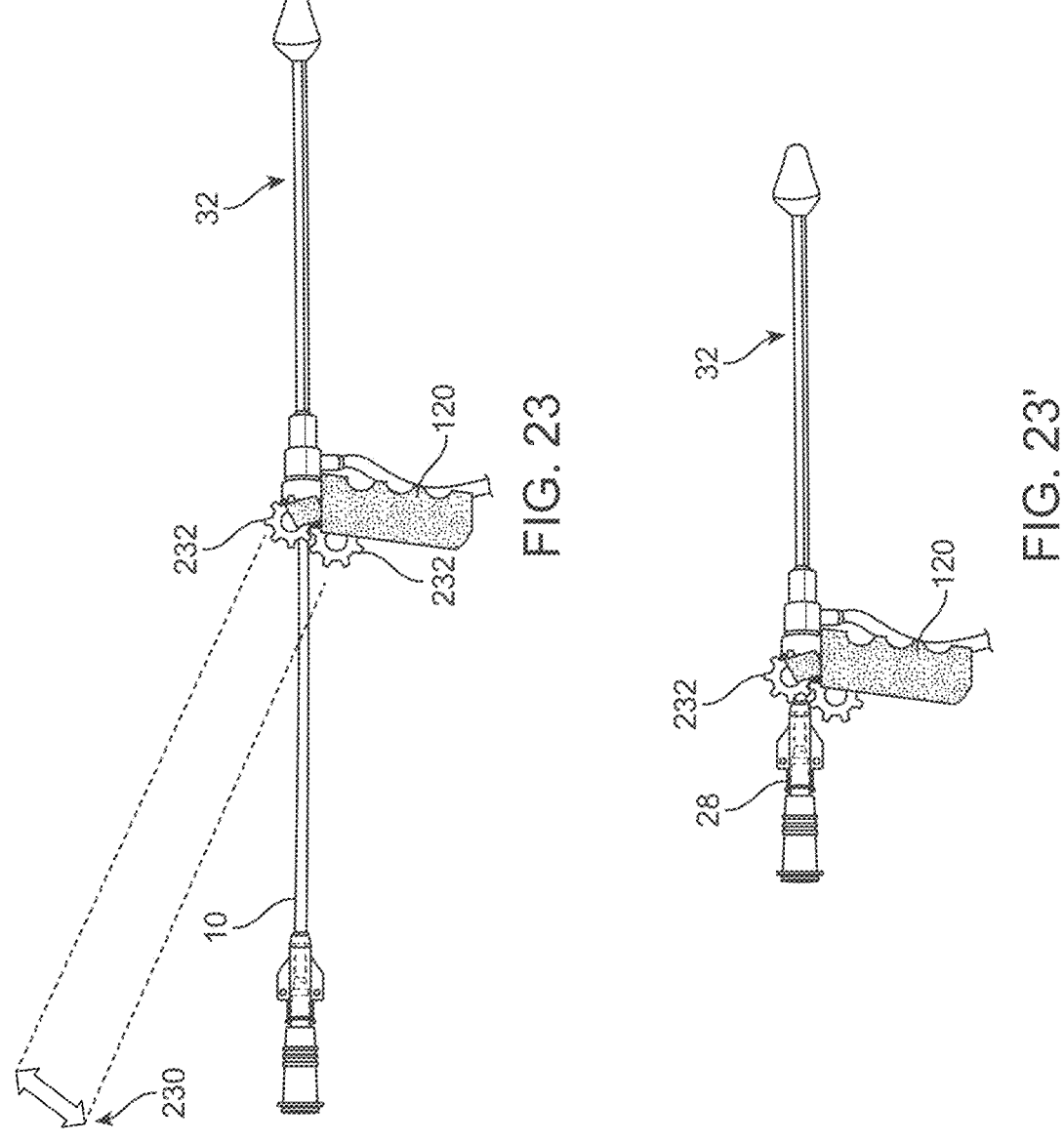
FIGS. 23 and 23' illustrate a variation of the everting catheter system having a controller that can advance and retract both the inner catheter and the embryo transfer catheter.

FIGS. 23 and 23' illustrate that the controller 118 that can advance and retract both the inner catheter 10 and the embryo transfer catheter 28 can have controller wheels 230 or gears 232. The controller wheels 230 can engage the inner catheter 10 for the entire advancement until the inner catheter 10 abuts the Y-fitting 50 of the everting catheter system 106. The controller wheels 230 can be spring-loaded, for example, to allow the controller wheels 230 to expand apart or enlarge (when analyzed as a single component together), as shown by arrows in FIG. 23, and allow the proximal luer hub to pass through the wheels and stop at the completion of the eversion process. At the point in the IVF procedure, the embryo transfer catheter 28 can be passed through the central lumen of the inner catheter 10 and into the uterine cavity. The controller wheels 230 can be configured to engage the distal end of the embryo transfer catheter 28, or in the case of an embryo transfer catheter 28 with a proximal portion with a larger outer diameter, the controller wheels 230 can engage the larger outer diameter portion. The controller wheels 230 can then advance and retract the embryo transfer catheter 28.

FIG. 23 illustrates that the controller 118 wheels can be spring-loaded to expand and contract to accommodate the varying outer diameters of the inner catheter 10, hub, and embryo transfer catheter 28, for example as some or all of the elements pass between the controller 118 wheels.

FIG. 23' illustrates that the controller 118 wheels can expand then re-coil due to spring loading for advancing and retracting the embryo transfer catheter 28.

U.S. Provisional Application Nos. 61/902,742, filed Nov. 11, 2013, 61/977,478, filed Apr. 9, 2014; 62/005,355, filed May 30, 2014, 62/007,339, filed Jun. 3, 2014, 62/528,422, filed Jul. 3, 2017, and 62/553,057, filed Aug. 31, 2017; U.S. patent application Ser. No. 16/029,305, filed Jul. 6, 2018; International Patent Application No. PCT/US18/49234, filed Aug. 31, 2018; and U.S. Pat. No. 9,028,401, issued May 12, 2015 and Ser. No. 10,034,986, issued Jul. 31, 2018, are incorporated by reference herein in their entireties, and any elements described therein can be used in combination with any of the elements in this application.

Any elements described herein as singular can be pluralized (i.e., anything described as "one" can be more than one). Any species element of a genus element can have the characteristics or elements of any other species element of that genus. The media delivered herein can be any of the fluids 70 (e.g., liquid, gas, or combinations thereof) described herein. The patents and patent applications cited herein are all incorporated by reference herein in their entireties. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

We claim:

1. A method for delivering matter into a uterine cavity, wherein the matter comprises a material that has an effect on reproduction, comprising:

everting a balloon in a cervical canal, wherein the balloon is attached to a first catheter, and wherein everting comprises pulling the first catheter distally through the cervical canal;

transporting a flexible tip guidance wire through the first catheter into the uterine cavity to direct a distal end of the everting balloon towards a targeted region, wherein the flexible tip guidance wire is advanced upon reduction of an internal pressure of the balloon;

transporting a second catheter holding the matter after access to the targeted region is reached; and delivering the matter from the second catheter into the uterine cavity.

2. The method of claim 1, wherein the matter comprises a device.

3. The method of claim 1, wherein the matter comprises a hormone.

4. The method of claim 1, wherein the matter comprises an agent for affecting embryo implantation and/or adherence to the uterine endometrium.

5. The method of claim 1, wherein the matter comprises a therapeutic agent.

6. The method of claim 1, wherein the matter comprises a device and a hormone.

* * * * *